US012663412B2

(12) United States Patent  
Coon et al.

(10) Patent No.: US 12,663,412 B2  
(45) Date of Patent: Jun. 23, 2026

(54) TOILET, TESTING, AND MONITORING SYSTEMS

(71) Applicant: WISCONSIN ALUMNI RESEARCH FOUNDATION, Madison, WI (US)

(72) Inventors: Joshua Coon, Middleton, WI (US); Michael Westphall, Fitchburg, WI (US); Ian Miller, Madison, WI (US); Lloyd Smith, Madison, WI (US); Keaton Mertz, La Jolla, CA (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 611 days.

(21) Appl. No.: 18/074,060

(22) Filed: Dec. 2, 2022

(65) Prior Publication Data

US 2023/0096779 A1    Mar. 30, 2023

Related U.S. Application Data

(63) Continuation of application No. PCT/US2021/035704, filed on Jun. 3, 2021.

(Continued)

(51) Int. Cl.  
*G01N 33/493* (2006.01)  
*E03D 11/11* (2006.01)  
(Continued)

(52) U.S. Cl.  
CPC ............ *G01N 33/493* (2013.01); *E03D 11/11* (2013.01); *E03D 13/005* (2013.01); *G01N 35/04* (2013.01); *G01N 2035/0401* (2013.01)

(58) Field of Classification Search  
CPC ........ G01N 21/75; G01N 21/77; G01N 31/22; G01N 33/48; G01N 33/483; G01N 33/487;  
(Continued)

(56) References Cited

U.S. PATENT DOCUMENTS

| | | | |
|---|---|---|---|
| 5,071,623 A | 12/1991 | Akutsu | |
| 5,184,359 A | 2/1993 | Tsukamura et al. | |

(Continued)

FOREIGN PATENT DOCUMENTS

| | | | |
|---|---|---|---|
| CN | 104790487 A | * | 7/2015 |
| CN | 205786649 U | * | 12/2016 |

(Continued)

OTHER PUBLICATIONS

Seung-min Park et al. "A mountable toilet system for personalized health monitoring via the analysis of excreta". Apr. 6, 2020. www.nature.com.

*Primary Examiner* — Jonathan M Dunlap  
(74) *Attorney, Agent, or Firm* — Seager, Tufte & Wickhem LLP

(57) ABSTRACT

Systems for monitoring metabolites may include a sample collection system and a urinalysis system of or for a toilet. The sample collection system may be automated to collect sample urine from a toilet or toilet area, transport the sample to the urinalysis system, and/or the sample urine for analysis at a later time or after analysis by the urinalysis system. The urinalysis system may be automated by proactively providing test material on which a subject may provide a urine sample. Once the urine sample has been provided the urinalysis system may provide the test material to an analyzer for analysis. Results of the analysis of the test material and sample urine may be provided to a mobile device of the subject and/or a remote server. The urinalysis system may provide a urine sample to a mass spectrometry unit for analysis.

19 Claims, 21 Drawing Sheets

Related U.S. Application Data

(60) Provisional application No. 63/035,275, filed on Jun. 5, 2020.

(51) Int. Cl.
   E03D 13/00 (2006.01)
   G01N 35/04 (2006.01)

(58) Field of Classification Search
   CPC ................. G01N 33/493; G01N 35/04; G01N 2021/7756; G01N 2021/7759; G01N 2021/7763; G01N 2021/7766; G01N 2030/062; G01N 2035/0401; G06T 7/0012; G06T 7/20; G06T 7/90; G06T 2207/10012; G06T 2207/10021; G06T 2207/10024; G06T 2207/20084; G06T 2207/30004; A47K 17/00; E03D 5/014; E03D 5/105; E03D 11/02; E03D 11/11; E03D 13/00; E03D 13/005; A61B 5/0077; A61B 5/1171; A61B 5/1172; A61B 5/14507; A61B 5/207; A61B 5/42; A61B 5/6891; A61B 10/0045; A61B 10/007
   See application file for complete search history.

(56) References Cited

U.S. PATENT DOCUMENTS

| | | | |
|---|---|---|---|
| 5,730,149 | A | 3/1998 | Nakayama et al. |
| 7,645,080 | B2 * | 1/2010 | Toji ........................ G03B 17/02 |
| | | | 348/360 |
| 11,604,177 | B1 * | 3/2023 | Park ........................... G06T 7/90 |
| 12,174,601 | B2 * | 12/2024 | Douglas ................. G16H 10/60 |
| 2015/0359522 | A1 * | 12/2015 | Recht ................... G01N 21/255 |
| | | | 600/573 |
| 2017/0322197 | A1 * | 11/2017 | Hall ..................... G01N 33/493 |
| 2018/0206772 | A1 * | 7/2018 | Hall ........................ A61B 5/201 |
| 2018/0321218 | A1 | 11/2018 | Hall et al. |
| 2019/0090859 | A1 | 3/2019 | Recht et al. |
| 2021/0158572 | A1 * | 5/2021 | Ko ........................... G01J 3/462 |
| 2024/0201174 | A1 * | 6/2024 | Wentink .............. G01N 33/493 |

FOREIGN PATENT DOCUMENTS

| | | | | | |
|---|---|---|---|---|---|
| CN | 107315003 | A | * | 11/2017 | ............. G01N 21/78 |
| CN | 108562548 | A | * | 9/2018 | .......... G01N 21/251 |
| CN | 109212177 | A | * | 1/2019 | ............. G05B 19/04 |
| CN | 208367020 | U | * | 1/2019 | |
| WO | WO-2020174063 | A1 | * | 9/2020 | ......... A61B 5/14507 |

* cited by examiner

TOILET, TESTING, AND MONITORING SYSTEMS

CROSS REFERENCE TO RELATED APPLICATIONS

This application is a continuation of International Application No. PCT/US2021/035704, filed on Jun. 3, 2021, which claims the benefit of U.S. Provisional Patent Application Ser. No. 63/035,275 filed on Jun. 5, 2020, the disclosures of which are incorporated herein by reference.

STATEMENT REGARDING FEDERALLY SPONSORED RESEARCH OR DEVELOPMENT

This invention was made with government support under GM118110 awarded by the National Institutes of Health. The government has certain rights in the invention.

TECHNICAL FIELD

The present disclosure pertains to testing systems and assessment tools, and the like. More particularly, the present disclosure pertains to excreta (urine and/or feces) testing and assessment systems and systems implemented in or in conjunction with a toilet.

BACKGROUND

Clinical urine testing may be performed with a method called urinalysis. Urinalysis may involve routine clinical tests that are used all over the world in human and veterinary medicine to check health conditions of a subject providing a urine sample. Urinalysis can measure a variety of important health metric, such as kidney and liver functions. An example urinalysis test may be a colorimetric test that typically performs 10-15 quantitative measurements, including tests of: hydration, glucose, creatinine, pH, ketones, bilirubin, urobilinogen, nitrite, blood, leukocytes, etc. Of the known approaches and systems for testing excreta and monitoring results of the testing, each has certain advantages and disadvantages.

SUMMARY

This disclosure is directed to several alternative designs for, devices of, and methods of using testing systems and assessment tools. Although it is noted that testing approaches and systems are known, there exists a need for improvement on those approaches and systems.

A first example is a toilet system. The toilet system comprises a toilet defining a basin for receiving urine from a subject and an automated urinalysis system. The automated urinalysis system comprises a test material holder configured to expose a test material to a sample of urine from the subject, a sample sensing device configured to ensure the test material is exposed to the sample of urine, and an analyzer configured to receive the test material after the sample sensing device ensures the test material has been exposed to the sample of urine.

Alternatively or additionally to any of the examples above, the sample sensing device is configured to ensure the test material is exposed to the sample of urine for a predetermined amount of time.

Alternatively or additionally to any of the examples above, the sample sensing device is configured to ensure the test material is exposed to a predetermined amount of the sample of urine.

Alternatively or additionally to any of the examples above, the analyzer comprises one or more image capturing devices configured to image the test material after the test material has been exposed to the sample of urine.

Alternatively or additionally to any of the examples above, the toilet system further comprises a cartridge comprising a plurality of test materials, and wherein one or more test materials of the plurality of test materials is loaded onto the test material holder.

Alternatively or additionally to any of the examples above, the test materials of the plurality of test materials comprise paper test strips reactive to metabolites in urine.

Alternatively or additionally to any of the examples above, the test materials of the plurality of test materials comprise urinalysis test cups.

Alternatively or additionally to any of the examples above, the toilet system further comprises a temperature sensing device configured to sense a temperature of the sample of urine.

Alternatively or additionally to any of the examples above, the toilet system further comprises a subject sensor configured to sense a subject at or approaching the toilet, and wherein the test material holder is configured to extend in response to the subject sensor sensing the subject at or approaching the toilet.

Alternatively or additionally to any of the examples above, the testing system further comprises a controller in communication with the test material holder, the sample sensing device, and the analyzer, and wherein the controller is configured to receive an indication the test material has been exposed to the sample of urine and output a control signal to cause the test material holder to provide the test material to the analyzer for testing.

Alternatively or additionally to any of the examples above, the controller is configured to output results of the analyzer testing the test material to a remote device.

Alternatively or additionally to any of the examples above, the toilet is a urinal.

A second example is an automated urinalysis system. The automated urinalysis system comprises a test material holder configured to expose a test material to a sample of urine from a subject, a sample collection unit configured to collect a predetermined volume of the sample of urine for exposure to the test material, an analyzer configured to receive the test material after the test material is exposed to the predetermined volume of the sample of urine, a controller in communication with the test material holder and the analyzer, and wherein the controller is configured to cause the test material holder to provide the test material to the analyzer after the test material has been exposed to the sample of urine.

Alternatively or additionally to any of the examples above, the sample collection unit includes a funnel shaped portion configured to deliver the predetermined volume of the sample of urine to the test material and cause additional urine to overflow the sample collection unit.

Alternatively or additionally to any of the examples above, the automated urinalysis system further comprises a cartridge comprising a plurality of test materials, and wherein a test material of the plurality of test materials is loaded onto the test material holder.

Alternatively or additionally to any of the examples above, the test material holder comprises a conveyor.

Alternatively or additionally to any of the examples above, the conveyor is configured to transport the test material from a sample receiving area to an analysis area.

Alternatively or additionally to any of the examples above, the test material comprises a test cup.

Alternatively or additionally to any of the examples above, the analyzer is configured to perform a colorimetric test on the test material using one or more image capturing devices.

A third example is a toilet system. The toilet system comprises a toilet, a liquid chromatography mass spectrometry (LCMS) unit, a sample collector at least partially positioned within the toilet, the sample collector configured to at least partially define a sample collection area and a flush area, a sample flow path in fluid communication with the LCMS unit and the sample collection area, and wherein the LCMS unit is configured to withdraw a predetermined amount of sample fluid from the sample flow path and perform an analysis on the predetermined amount of sample.

Alternatively or additionally to any of the examples above, the toilet system further comprises a pump configured to pump sample urine from the sample collection area through the sample flow path and into the flush area.

Alternatively or additionally to any of the examples above, the toilet system further comprises a valve system in communication with the sample flow path and configured to control a flow of sample fluid to the LCMS unit.

A fourth example is a sample collection system. The sample collection system comprises a sample collector configured to be positioned at least partially within a toilet, the sample collector defining a sample collection portion, a pumping system, a sample flow line in fluid communication with the pumping system and the sample collection portion, and a sample storage system in communication with the sample flow line, the sample storage system is configured to receive a sample from the sample collection portion via the sample flow line and store the sample received.

Alternatively or additionally to any of the examples above, the pumping system comprises a first pump configured to pump a sample from the sample collection portion to the sample storage system.

Alternatively or additionally to any of the examples above, the first pump is a syringe pump.

Alternatively or additionally to any of the examples above, the pumping system comprises a second pump configured to pump a sample from the sample collection portion through the sample flow line and pump fluid from the sample storage system through a waste fluid line.

Alternatively or additionally to any of the examples above, the second pump is a peristaltic pump.

Alternatively or additionally to any of the examples above, the sample collection system further comprises a valve system in communication with the sample flow line and configured to control a flow of sample fluid to the sample storage system.

Alternatively or additionally to any of the examples above, the sample collector includes a cleansing flow path configured to be in communication with a cleansing fluid line and configured to direct cleansing flow from the cleansing fluid line to the sample collection portion.

Alternatively or additionally to any of the examples above, the sample collector includes a waste flow path configured to be in communication with a waste fluid line from the pumping system.

Alternatively or additionally to any of the examples above, the sample storage system is configured to separately store a plurality of samples.

Alternatively or additionally to any of the examples above, the sample storage system is configured to provide temperature control of the sample stored. The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
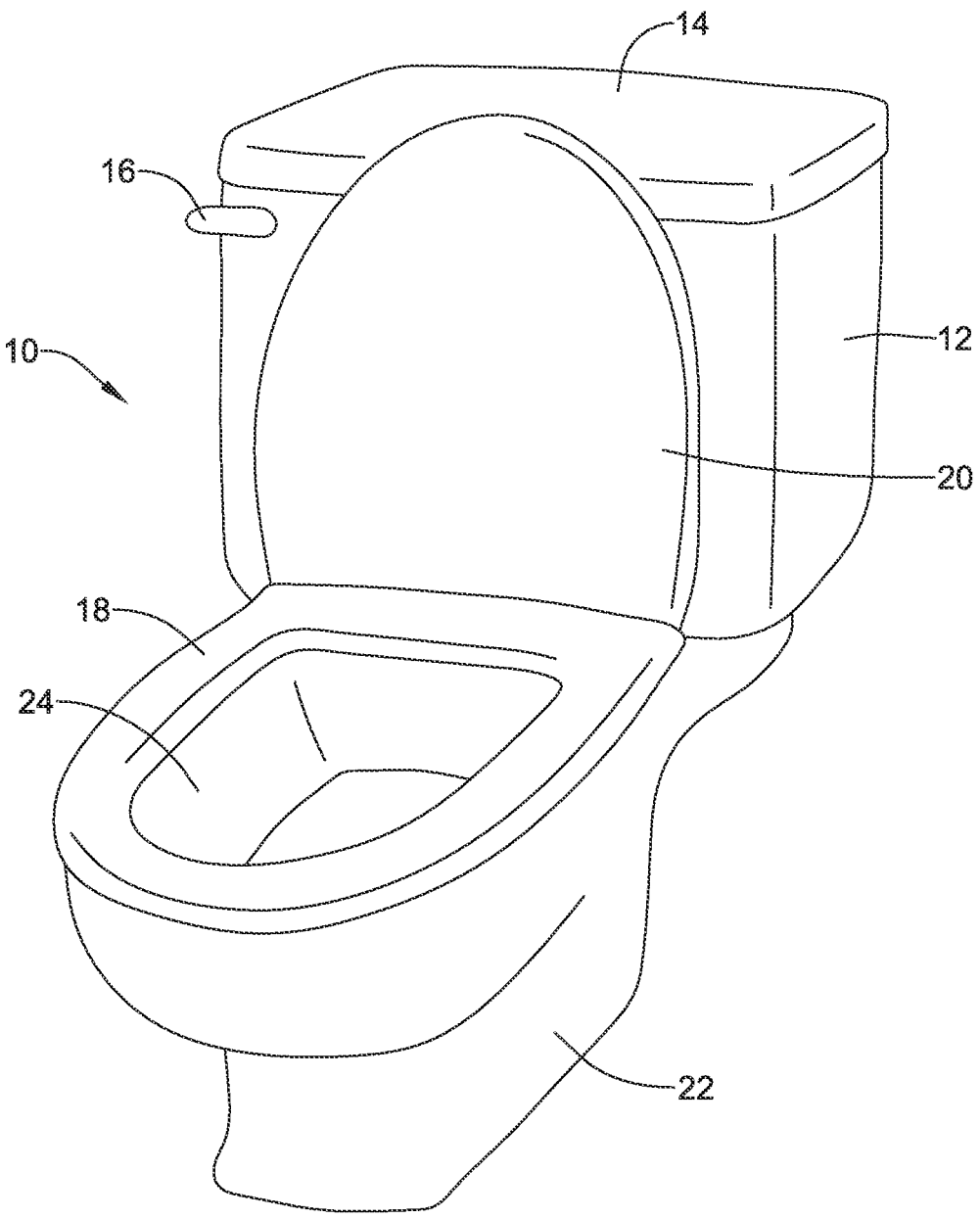
FIG. 1 is a schematic perspective view of an illustrative toilet.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges, and/or values pertaining to various components, features, and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Current medical practice is often reactive. Annual check-ups measure only a few basic phenotypes and may not (e.g., fail to or are unable to) predict serious health threats such as cancer, dementia, or exposure to pathogens. Instead, disease often may not be detected until critical symptoms present, which is often too late for meaningful or cost-effective intervention. Owing to a lack of data, the current model of healthcare is periodic and geared to manage disease symptoms at their onset rather than preventing or reversing the underlying etiology. It has been found that humans and medical practice, in general, could benefit from technology integrated into daily life that facilitates quantifying baseline wellness metrics and monitoring for and/or of deviations from those baseline wellness metrics. In one example, technology integrated into daily life that facilitates measuring physiological phenotypes, such as the urinalysis systems and techniques discussed herein, may provide data valuable for quantifying and monitoring baseline wellness of subjects.

Generally, there are currently two avenues for continuous or longitudinal monitoring of health and disease: (1) consumer-grade wearables and (2) clinical-based precision medicine. Wearable devices such as smart watches are broadly accessible and increasingly popular as consumer products. Data from these devices has the advantage of being continuously and passively collected, triggering wide scale adoption. Many companies have devoted significant resources to leverage tools in big data and artificial intelligence (AI) to provide actionable insights from these popular products. In one example, Apple (CA, USA) has recently received FDA approval to provide users with alerts to detect atrial fibrillation. This diagnostic capability was made possible by widespread consumer participation in the Apple Heart Study and a follow-up clinical trial, which provided expansive datasets to train AI models.

Given sufficiently large datasets, heart rate information alone can suggest the onset of diverse disease processes. However, this type of data offers little information on the origins, mechanisms, and progression of disease. For instance, while an elevated resting heart rate may indicate a number of adverse medical events, including an infection, such data is not able to distinguish between bacterial and viral infections. This lack of mechanistic information leaves patients and health care providers unable to implement targeted therapeutic intervention and, in this case, antibiotic stewardship.

On the other end of the spectrum of longitudinal monitoring are tools for clinically-based precision medicine. These tools include, but are not limited to, deep genome sequencing and integration with multidimensional clinical phenotypes such as transcriptomics, proteomics, metabolomics, and metagenomics datasets. There are a number of large-scale efforts underway to provide multi-omic phenotyping for large cohorts. Examples of such efforts include the Pioneer 100 Wellness Project and the NIH All of Us program. While these efforts have proven to successfully leverage diverse physiological datasets to enable meaningful intervention, they remain hampered by their relative inaccessibility and periodic nature. In other words, while high quality data from clinically based precision medicine provide clinically actionable insights, the data is expensive, invasive, and difficult to collect, resulting in collections that may occur monthly rather than daily, for example.

Modern medicine has the opportunity to be more effective as it transitions from reactive disease care to a framework that is predictive, preventive, personalized, and participatory. To combine the accessibility of wearable devices with the robustness and quality of clinical medicine, a third option, real-time metabolic phenotyping, has been developed that provides quantitative measurements of health and mechanistic insights into the origins and progression of disease. Real-time metabolic phenotyping (e.g., "metabolomics") may provide a quantitative fingerprint of metabolic health of a subject along with information about exposure to toxins, drugs, and pathogens.

Continuous or longitudinal (e.g., daily, weekly, etc.) metabolic measurements may be collected at home, in the workplace, and/or one or more other suitable locations to provide molecular insights into underlying disease processes, such as distinguishing between patients with related strains of infectious bacteria, as well as quantifying the effect of lifestyle decisions on health and disease. Lifestyle factors such as nutrition, alcohol and tobacco usage, sleep, and physical activity are well known to contribute to the risk for chronic disease, which costs the United States alone $2.97 Trillion a year, or 90% of all healthcare expenditures. By empowering subject participation in their own medical care with actionable information and disease classification using a continuum of molecular phenotypes rather than discrete clinical symptoms, the cost and efficacy of healthcare could be dramatically improved.

While a number of biological matrices, including saliva, blood and feces, could be used as a source of metabolic information for metabolomics, urine offers some key advantages as it can be easily collected passively, non-invasively, and longitudinally (e.g., continuously over time). Further, urine is a rich source of cellular metabolites, most stemming from filtration of blood in the kidneys, which filter about a half cup of blood every minute.

Urine has long been recognized as a rich fluid for medical diagnostics and presently many clinical assays are performed on this biological fluid. Approximately 4,500 metabolites have been documented in urine, showing connections to approximately 600 human conditions including but not limited to: obesity, cancer, inflammation, neurological disease, and infectious disease. Further, pregnancy, ovulation, urinary tract infection, diet, and exercise induce metabolomic signatures that can be observed in urine. Additionally, many drugs and associated metabolites are readily detected from urine. As such, urine testing and/or monitoring may present opportunities for tailoring drug dosages to individuals, monitoring compliance with prescribed drug dosages, monitoring drug usage, monitoring risk factors of drug usage, providing effective stratification for clinical trials (e.g., which can greatly reduce the cost of pharmaceutical development), etc.

Patients with diabetes are an example population that may particularly benefit from on-going urinalysis, as such patients are at an increased risk of developing kidney disease and may be taking treatments having side effects that put patients at risk for other diseases and complications. One example treatment for patients with diabetes is JARDIANCE™, which may be used to lower the risk of cardiovascular disease for diabetes patients, but also increases the risk of developing UTIs, kidney damage, and ketone bodies. All of these risk factors could be continuously monitored with urinalysis systems. Thus, a passive, continuous, and in-home diagnostic could serve as an ideal and cost-effective companion medical device for modern diabetes therapeutics.

Urinalysis may be utilized to test and/or monitor metabolites in a subject's urine. Standard urinalysis tests (e.g., colorimetric urinalysis tests) may be configured to indicate, measure, and/or monitor kidney function, liver function, hydration, a presence of a urinary tract infection (UTI), diabetes, pregnancy, fertility, drug usage (e.g., including, but not limited to, alcohol usage), etc. Colorimetric urinalysis tests may perform 10-15 quantitative measurements at a time, including, but not limited to, tests of: glucose, creatinine, pH, ketones, bilirubin, urobilinogen, nitrite, blood, and leukocytes, etc. Colorimetric chemistry used in urinalysis may be rapid (e.g., results can be obtained and interpreted in minutes) and may be generally based on the production of a chromogenic compound following the interaction of molecules in urine with a dipstick reagent. For example, glucose and hemoglobin—which can reflect the presence of blood in urine—produce chromogenic compounds in the presence of peroxidases in a test strip. Additional and/or alternative test strip colorimetric chemistry may be based on oxidation-reduction reactions, the binding of dye compounds, antibody binding, etc. The intensity of color change can then be used to quantify levels of a given compound of interest.

Colorimetric testing of other target analyte is available. SHERLOCK (an acronym for Specific High-Sensitivity Enzymatic Reporter UnLOCKing) is one such example and is based on CRISPR-Cas13a to detect attomolar concentrations of specific nucleic acid sequences directly from blood or urine samples. The transitive value of the SHERLOCK technology may lie in its sensitivity, specificity, and simplicity. For example, SHERLOCK technology is inexpensive to manufacture, can be deployed as a point of care diagnostic, and all required reagents may be lyophilized and incorporated directly into a paper test strip with long term stability. This SHERLOCK technology may enable one to target diagnostic nucleic acid sequences, such as those from specific microorganisms, viruses, or other diagnostics transcripts capable of monitoring and diagnosing a wide array of disease. In a toilet environment, the simplified testing of the SHERLOCK technology may be used to transform a current model of testing feces (e.g., in which feces samples are sent to a laboratory for processing) by instead utilizing a relevant test strip in a toilet implemented testing and monitoring system based on the SHERLOCK technology.

To facilitate longitudinal monitoring of metabolites of a patient and/or predictive medicine, a testing and/or monitoring system may be implemented in or with a toilet to create a toilet system. For example, at least part of the testing and/or monitoring system may be implemented in a toilet, in a toilet seat of or attached to a toilet, and/or as an attachment to a toilet or a toilet set. In one example of a testing and/or monitoring system implemented in or with a toilet, the testing and/or monitoring system may be configured to provide a test material in direct contact with urine, perform an analysis of the urine in contact with the test material at or adjacent the toilet, and transmit the resulting data from the analysis via a wired and/or wireless connection to a smart device and/or database to facilitate temporal tracking and/or data related to tested urine.

Using such an implemented urinalysis testing and/or monitoring system may allow for multiple intra-day measurements that could be utilized to quantify and/or control for diurnal effects in predictive machine learning models. Further, in some cases, integration of data from the urinalysis testing and/or monitoring systems may be integrated with one or more other suitable data streams including, but not limited to, electronic health records, fitness application data (e.g., data from applications on mobile devices that may record heart rate, heart rate variability, step count, sleep, nutrition, GPS coordinates, etc.) to measure and predict health conditions of the subject and/or provide specific products and/or behavioral/activity recommendations. In one example, integration of nutritional consumption, geospatial information, and metabolite data from urinalyses over time may identify certain foods, activities, or locations associated with an upregulation in inflammatory processes of the subject. Additionally, for competitive athletes urinalysis testing and/or monitoring may provide a metabolic signature of rest and recovery that could be used to set an intensity and/or type of workout to be performed on a given day in order to maximize performance on a day in the future (e.g., on game day).

Turning to the Figures, FIG. 1 depicts a schematic perspective of an illustrative toilet 10 in which or with which a urinalysis system may be implemented. The illustrative toilet 10 depicted in FIG. 1 may include a tank 12, a tank lid 14, a handle 16 adjustable to flush the toilet 10, a seat 18, a seat lid 20, a base 22, and a basin 24 at least partially defined by the base 22. Although FIG. 1 depicts the toilet 10 as a standard tank toilet, the toilet 10 may be a tankless toilet, a urinal, a pressure assisted toilet, a gravity-feed toilet, a double cyclone toilet, a waterless toilet, and/or other suitable type of toilet. The toilet 10 is depicted in the Figures as being various types of toilets.

A urinalysis system may be configured to be used in or with a toilet (e.g., the toilet 10 and/or other suitable toilet) and may include suitable components for obtaining a sample to be tested and performing the testing. In some cases, the urinalysis system may be entirely or at least partially built into the toilet 10 (e.g., built into the base 22, the lid 20, and/or other suitable portion of the toilet 10) and/or retrofitted to the toilet as or as part of a replacement component (e.g., a replacement seat, replacement drain pipes, etc.) and/or as a component attachable to the toilet 10.

Figure 2:
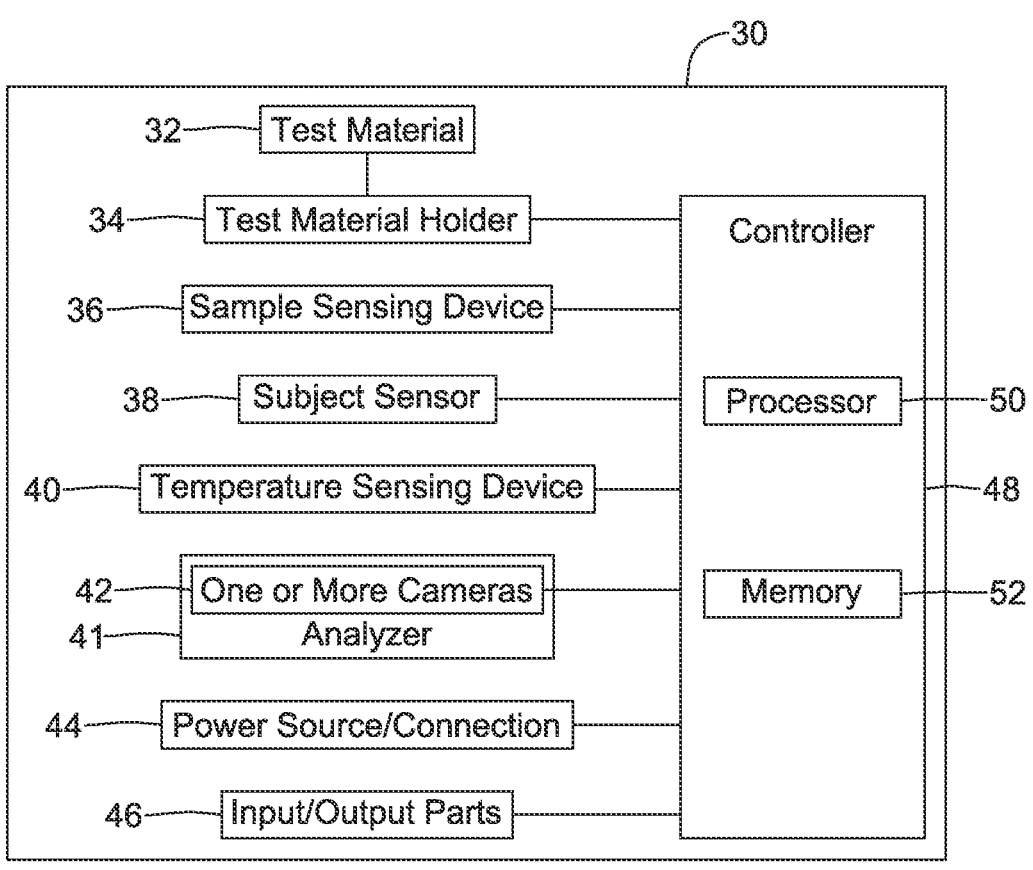
FIG. 2 is a schematic box diagram of an illustrative urinalysis system.

FIG. 2 depicts a schematic box diagram of an illustrative urinalysis system 30 (e.g., an automated urinalysis system) that may be incorporated into the toilet 10 and/or used with the toilet 10. As depicted in FIG. 2, an illustrative urinalysis system 30 may include, but is not required to and is not limited to, test material 32, one or more test material holders 34, one or more sample sensing devices 36, one or more subject sensors 38, one or more temperature sensing devices 40, one or more analyzers 41, one or more cameras 42 (e.g., one or more image capturing devices), one or more power sources/connections 44, one or more input/output ports 46, one or more controllers 48, and/or one or more additional or alternative components suitable for use in an urinalysis system. In some cases, the controller 48 may include, among other components, a processor 50 and memory 52 configured to store data and/or instructions executable by the processor 50 to perform one or more methods or techniques discussed herein and/or otherwise. Optionally, the urinalysis system 30 may include a user interface including one or more of a display, a remote display, an input component (e.g., a keypad, keyboard, mouse, touch pad, touchscreen, etc.), a speaker, a microphone, and/or other suitable component for interacting with features of the urinalysis system 30. Further, although FIG. 2 depicts various components of an illustrative urinalysis system 30, fewer, additional, and/or alternative components, may be used in a urinalysis system that is consistent with this disclosure.

The test material 32 of the urinalysis system 30 may be any suitable test material for obtaining a sample of and/or reacting with urine from a subject. In one example, the test material 32 may be test trips (e.g., paper test strips and/or other suitable material). In a further example, the test material 32 may be testing cups. In some cases, the test material 32 may be stored in a cartridge in, attached to, or attachable to the toilet 10. In some cases, the cartridge may be re-fillable with the test material 32 and/or may be replaced with a cartridge loaded with test material 32. The test material 32 may include a target thereon to facilitate a user accurately providing a urine sample, but this is not required.

The test material 32 may be configured to detect, sense, and/or measure metabolites for one or more diagnostics usable in determining and/or tracking the health of the subject. For example, the test material 32 may be configured to detect, sense, and/or measure one or more of leukocytes for identifying a urinary tract infection (UTI) and/or presence of bacteria; nitrites for identifying a UTI; urobilinogen for sensing liver function and indicating liver disease; a pH level for determining an acidic or alkaline state of the sample (e.g., the urine); a protein level for indicating possible kidney health issues; blood levels for identifying kidney stones and/or identifying if kidney stones are forming; ascorbate for identifying vitamin C levels in the sample; specific gravity for identifying how well kidneys are filtering and/or for the determining the glomerular filtration rate (GFR) of kidneys; ketones for indicating a subject providing the sample has diabetes and/or detecting acetoacetic changes in the sample; bilirubin for indicating liver and/or gallbladder issues; glucose for determining sugar in the sample; microalbumin for identifying kidney damage and/or determining kidney health; creatinine for determining kidney health and ensuring the kidneys are properly getting rid of creatinine in a subject's body; calcium for determining calcium levels associated with the subject's heart, kidneys, and thyroid; and/or one or more other suitable metabolites for identifying and/or determining the health of the subject. Further, the listed metabolites may be utilized individually and/or in combination for identifying and/or determining other suitable conditions of the subject. Additionally or alternatively, the test material 32 may be configured to detect a presence of substances in the sample from the subject. Example substances include, but are not limited to, alcohol, marijuana (THC), cocaine, opiates, methamphetamines, oxycodone, amphetamines, barbiturates, benzodiazepines, methadone, methlenedioxymethamphetamine (MDMA), phencyclidine (PCP), propoxyphene, performance enhancing drugs, etc. Further, test material 32 may be configured to determine or facilitate determining if the subject is pregnant and/or a fertility level of the subject. All of the metabolites and/or conditions discussed herein may be tested using a single testing material 32 and/or multiple testing materials 32 using one or more samples. Although the test material 32 may be configured to determine or identify the metabolites, substances, and conditions discussed herein, it is contemplated that the test material 32 may be configured to determine or identify other health related parameters.

The test material holder 34 may take on any suitable configuration for holding the test material 32 and capturing a sample from a subject. In one example, the test material holder 34 may be configured to load or be loaded with the test material 32 in any suitable manner (e.g., from a cartridge and/or other suitable storage at which the test material 32 is located). In one example, a conveyor system, which may or may not be part of the test material holder 34, may be utilized to load the test material holder 34 with the test material 32, but this is not required. The test material holder 34 may be configured to have minimal contact with loaded test material 32 and may be configured to facilitate directly exposing the test material 32 to urine from a subject. By minimally contacting the test material 32 and directly exposing the test material to urine, a likelihood of contamination of the test materials 32 and need for rigorous cleaning, beyond rinsing during a flush, of the test material holder 34 may be mitigated In some cases, the test material holder 34 may be and/or may include an extending component (e.g., a wand-like extension similar to a wand-like extension of a bidet) that may automatically extend in response to the urinalysis system 30 detecting a subject's approach to the toilet 10 and/or retract in response to detecting a suitable sample has been received. Alternatively or in addition, the test material holder 34 may be in fixed position and/or manually extended and/or retracted.

The subject sensor 38 may be configured to sense movement of a subject toward the toilet 10 and/or movement of the subject away from the toilet 10. The subject sensor 38 may be configured to sense one or more suitable parameters for determining a presence and/or movement of the subject. Example parameters the subject sensor 38 may sense include, but are not limited to, temperature, motion, etc. Further, in some cases the subject sensor 38 may be configured to send values related to the sensed one or more parameters to a controller (e.g., the controller 48 and/or other suitable controllers) to determine the presence and/or movement of the subject, to identify the subject, etc., but this is not required and the subject sensor 38 may be configured to determine the presence and/or movement of the subject based on the sensed one or more parameters.

In response to detecting the approach or presence of the subject at the toilet 10 based on outputs from the subject sensor 38, the test material holder 34 may be extended. In response to the subject sensor 38 detecting the subject moving away from the toilet 10, the test material holder 34 may be retracted. The test material holder 34, however, may be extended and/or retracted in response to one or more other parameters (e.g., an output of the sample sensing device 36, etc.), upon one or more determinations by the controller 48 and/or other suitable controllers, upon a signal from the subject or other user (e.g., a signal initiated by selection of an option or button to extend and/or retract the test material holder 34), and/or in response to a signal initiated in one or more other suitable manners.

The temperature sensing device 40 may be any suitable component configured to sense a parameter related to temperature. In one example, the temperature sensing device 40 may be or may include a thermocouple and/or one or more other suitable temperature sensing components. In some cases, the temperature sensing device 40 may be implemented in the test material holder 34, but this is not required in all cases. Additionally or alternatively to the temperature sensing device 40 being at least partially implemented in the test material holder 34, at least a portion of the temperature sensing device 40 may be implemented in the seat 18 and/or other portion of the toilet 10.

When at least partially incorporated in the test material holder 34 and/or other suitable portion of the toilet 10, the temperature sensing device 40 may be configured to sense a temperature of a sample (e.g., urine) from a subject. The urine temperature may be recorded in a database in memory of or in communication with the urinalysis system 30. In some cases, a body temperature of the subject providing the sample may be determined (e.g., calculated) from the urine temperature. When at least partially incorporated in the seat 18 and/or other suitable portion of the toilet 10, the temperature sensing device 40 may facilitate determining a body temperature of the subject providing a sample by contacting or scanning skin of the subject and the body temperature of the subject may be recorded in a database in memory of or in communication with the urinalysis system 30.

The sample sensing device 36 may be configured to detect when a sample has been received at the test material 32 (e.g., detect urination). In some cases, the sample sensing device 36 may be configured to detect when a sample has been received at the test material 32 through measuring one or more parameters related to conductivity, temperature, and/or other suitable parameters. Further, an adequate sample may be determined to have been received at the test material 32 by determining the sample has been received for a predetermined amount of time and/or a predetermined volume has been received. In one example, a detection of an adequate sample by the sample sensing device 36 may occur when it is determined that a current passes from a first electrode to a second electrode separated from a first electrode for a period of time due to the test material 32 continuously receiving a sample from the subject. In another example, a detection of an adequate sample by the sample sensing device 36 may occur when it is determined a temperature has reached and/or exceeded a threshold temperature for a predetermined amount of time. Further, in some cases the sample sensing device 36 may be configured to sense values of one or more parameters (e.g., conductivity, temperature, volume, flow rate, etc.) from which a controller (e.g., the controller 48 and/or other suitable controllers) may determine the presence of a sample, but this is not required and the sample sensing device 36 may be configured to determine the presence of a sample without a separate controller.

In response to the results of the sample sensing device 36 indicating a presence of an adequate sample at the test material 32, the test material holder 34 may be retracted. Once retracted and/or in the process of retracting, the test material holder 34 may load the test material 32 into an analyzer 41 for analyzing the sample and/or the test material 32.

The analyzer 41 may be configured to analyze and/or facilitate analyzing a sample from a subject that is received. In some cases, the test material 32 having a sample thereon from a subject may be received in and/or loaded into the analyzer 41 for analysis after an adequate sample has been received (e.g., as determined by the sample sensing device 36 and/or determined in one or more other suitable manners). In one example, the analyzer 41 may be configured to perform colorimetric testing on the test material 32 having a sample thereon. In another example, the analyzer 41 may be configured to perform a mass spectrometry analysis on received samples.

In some cases, the analyzer 41 may collect optical images of the test material 32 that received the sample from the subject. To facilitate collection of optical images of the test material 32, the analyzer 41 may include one or more cameras 42 for imaging the test material 32 that received the sample. Example types of cameras utilized by the analyzer 41 may include, but art not limited to, photodiode array imaging, photomultiplier tubes, video cameras, digital cameras, etc.

As discussed above with respect to the test material 32, the test material 32 may be configured to respond a particular way to certain metabolites and the cameras 42 of the analyzer 41 may be arranged to capture images of the test material 32 showing how the test material 32 responded to the received sample. Once optical images of the test material 32 are obtained, the analyzer 41 may analyze the images to determine the presence of certain pre-determined metabolites based on how the sample and/or the test material 32 reacted to one another. Alternatively or additionally, the optical images may be sent to a controller for analysis and determinations as to which metabolites are present in the sample.

After the images of the test material 32 have been captured and/or the test material 32 and the sample have been analyzed, the test material 32 may be discarded from the analyzer 41 (e.g., flushed down the toilet 10) and/or stored (e.g., for discarding, for record keeping, etc.) in the analyzer 41 and/or a compartment adjacent to the analyzer 41.

The power source/connection 44 may be any suitable component configured to power and/or facilitate powering one or more of the components of the urinalysis system 30. In one example, the power source/connection 44 may include circuitry, a cord, and a plug (e.g., a 110 volt (V) plug and/or other suitable plug) to facilitate transmitting power from a wall power supply to electrical or electronic components of the toilet 10 and/or the urinalysis system 30. Additionally or alternatively, the power source/connection 44 may include one or more replaceable or rechargeable batteries that may be utilized to power one or more components of the toilet 10 and/or the urinalysis system 30. In some cases, the power source/connection 44 may be configured such that a battery thereof may be able to power the urinalysis system 30 for several weeks, if not months, of routine use.

The input/output (I/O) ports 46 may be any type of communication port configured to communicate with components of the urinalysis system 30 including, but not limited to, the controller 48 and/or one or more components separate from the urinalysis system 30. Example types of I/O ports 46 may include wired ports, wireless ports, radio frequency (RF) ports, Bluetooth ports, Near-Field Communication (NFC) ports, HDMI ports, Ethernet ports, VGA ports, serial ports, parallel ports, component video ports, S-video ports, composite audio/video ports, DVI ports, USB ports, optical ports, and/or other suitable ports. In some cases, the I/O ports 46 may facilitate transmitting resulting data from the urinalysis system 30 to a remote device (e.g., a remote server, a subject's mobile device, etc.) and/or transmitting data to the urinalysis system 30 from a remote device in a wired and/or wireless manner.

The controller 48 may include one or more components. In one example, the controller 48 may include the processor 50, the memory 52, and/or one or more other suitable components of the urinalysis system 30. In some cases, the memory 52 may be or may include non-transitory computer readable medium that may include or may be programed to include software or other instructions to be executed by the processor 50 and facilitate the controller 48 operating in an automated manner to output control signals to the components of the urinalysis system 30 for analyzing a sample from a subject and/or output data, via the I/O ports 46 for example, to a remote device. Additionally or alternatively, the controller 48 may be configured to receive data and/or control signals from components of the urinalysis system 30 and/or from a remote device.

The processor 50 may include a single processor or more than one processor working individually or with one another. Example processor components may include, but are not limited to microprocessors, microcontrollers, multi-core processors, graphical processing units, and/or other suitable processors.

The memory 52 may include a single memory component or more than one memory component working individually or with one another. Example types of memory may include RAM, ROM, EEPROM, FLASH, other volatile or non-volatile memory, or any other suitable memory for the controller 48. The memory 52 may be or may include non-transitory computer readable medium.

Figure 3:
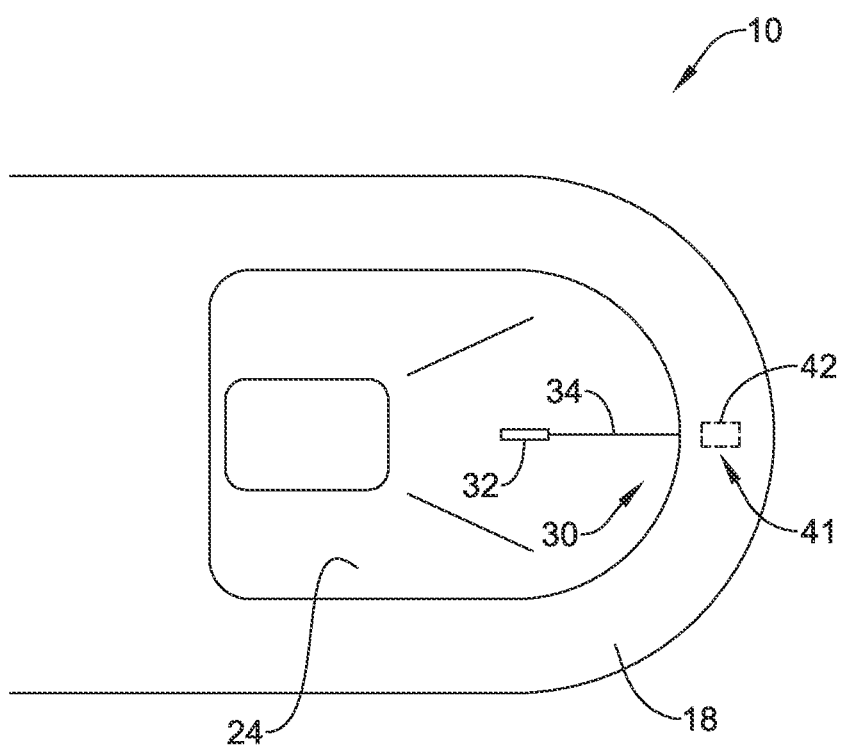
FIG. 3 is a schematic top view of a toilet incorporating an illustrative urinalysis system.

FIG. 3 depicts a schematic top view of a portion of the toilet 10 in which the urinalysis system 30 is implemented at least partially in the seat 18. As depicted in FIG. 3, the example configuration of the urinalysis system 30 includes the camera 42 (shown in broken lines to indicate it may be within and/or covered by a portion of the seat 18) of the analyzer 41, the test material 32, and the test material holder 34 located at a front of the toilet 10 or extending from a front of the toilet 10 over the basin 24 toward a back of the toilet 10. When extendable/retractable, the test material holder 34 may extend the test material 32 outward over the basin 24 to facilitate a subject providing a urine sample. In some cases, once a urine sample has been received at the test material 32, the test material holder 34 may be retracted back toward the seat 18 and/or into the seat 18 or at least into a footprint of the seat 18.

Figure 4:
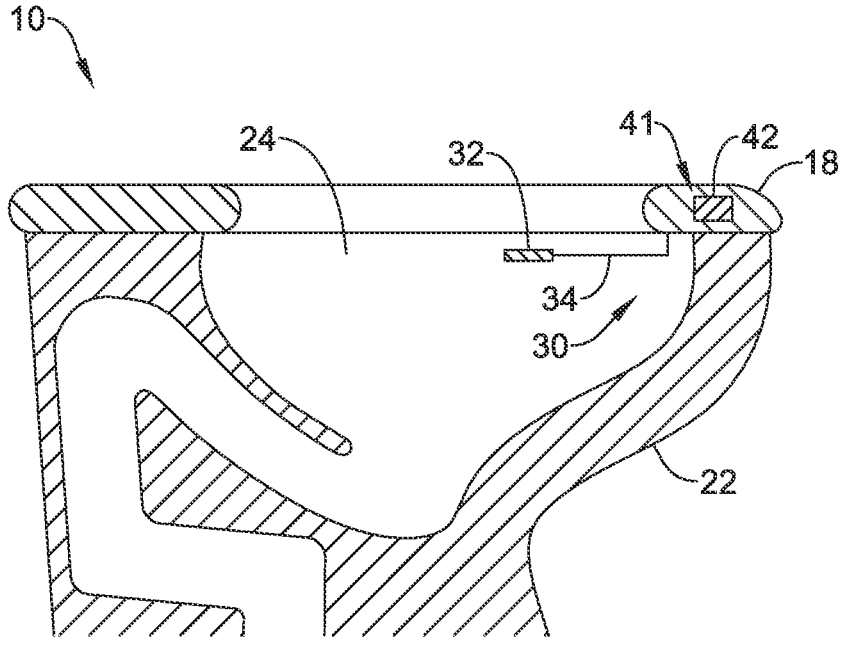
FIG. 4 is a schematic cross-section view of the toilet incorporating the illustrative urinalysis system, as depicted in FIG. 3.

FIG. 4 depicts a schematic cross-sectional view of the toilet 10 and urinalysis system 30 of FIG. 3. As depicted in FIG. 4, the test material holder 34 may extend from the seat 18 toward the back of the toilet 10 to position the test material 32 over the basin 24 for collecting a urine sample from a subject.

Figure 5:
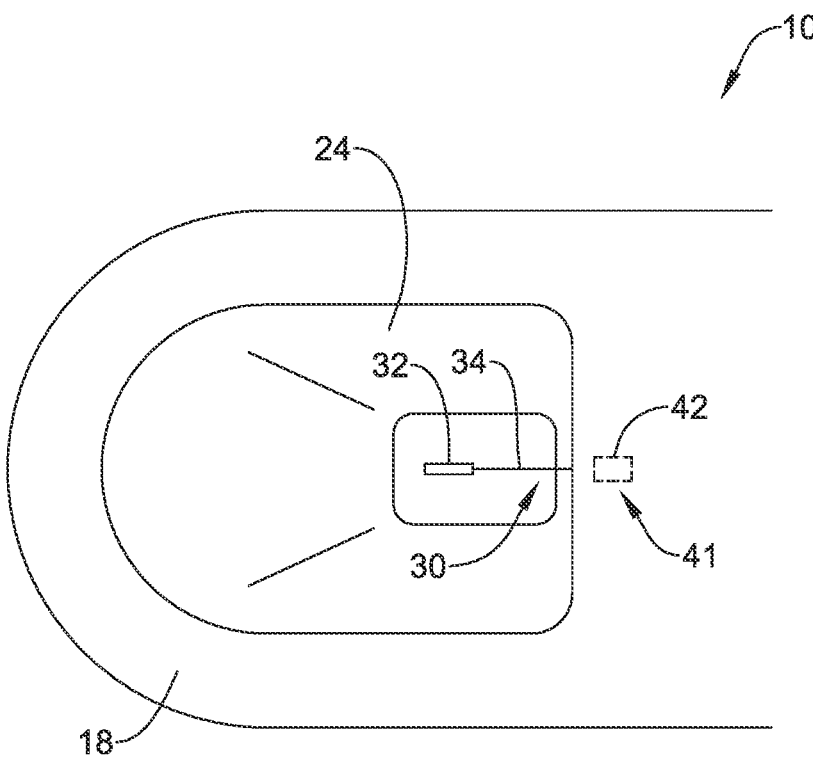
FIG. 5 is a schematic top view of a toilet incorporating an illustrative urinalysis system.

FIG. 5 depicts a schematic top view of a portion of the toilet 10 in which an example configuration of the urinalysis system 30 is implemented at least partially in the seat 18 similar to the view depicted in FIG. 3, but with the urinalysis system 30 at least partially located toward a back of the toilet 10. As depicted in FIG. 5, the camera 42 (shown in broken to indicate it may be within and/or covered by a portion of the seat 18) of the analyzer 41, the test material 32, and the test material holder 34 are located at the back of the toilet 10 or extending from the back of the toilet 10 over the basin 24 toward a front of the toilet 10. When extendable/retractable, the test material holder 34 may extend the test material 32 outward over the basin 24 to facilitate a subject providing a urine sample. In some cases, once a urine sample has been received at the test material 32, the test material holder 34 may be retracted back toward the seat 18 and/or into the seat 18 or at least into a footprint of the seat 18.

Figure 6:
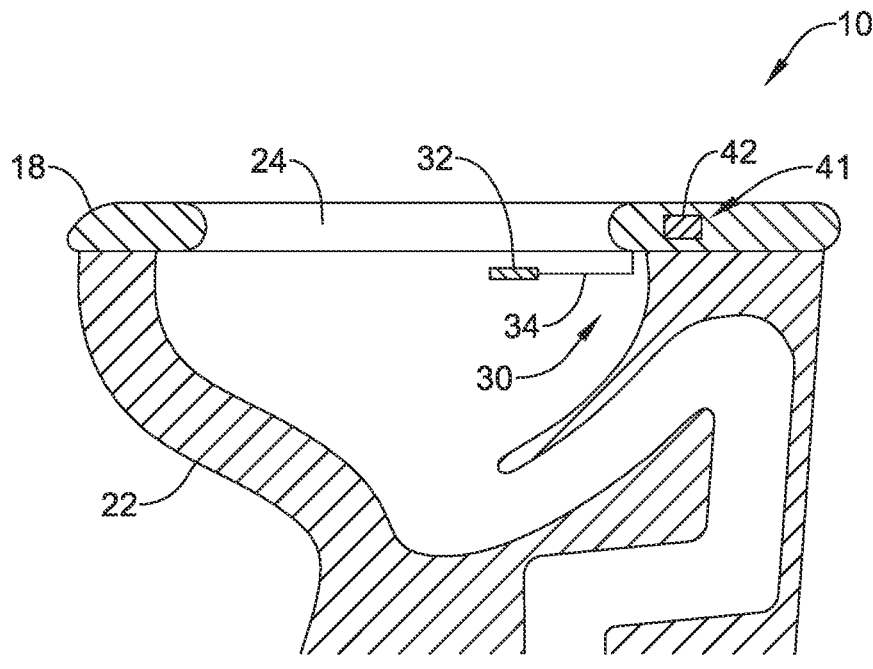
FIG. 6 is a schematic cross-section view of the toilet incorporating the illustrative urinalysis system, as depicted in FIG. 5.

FIG. 6 depicts a schematic cross-sectional view of the toilet 10 and the urinalysis system 30 of FIG. 5. As depicted in FIG. 6, the test material holder 34 may extend from the seat 18 toward the front of the toilet 10 to position the test material 32 over the basin 24 for collecting a urine sample from a subject.

Figure 7:
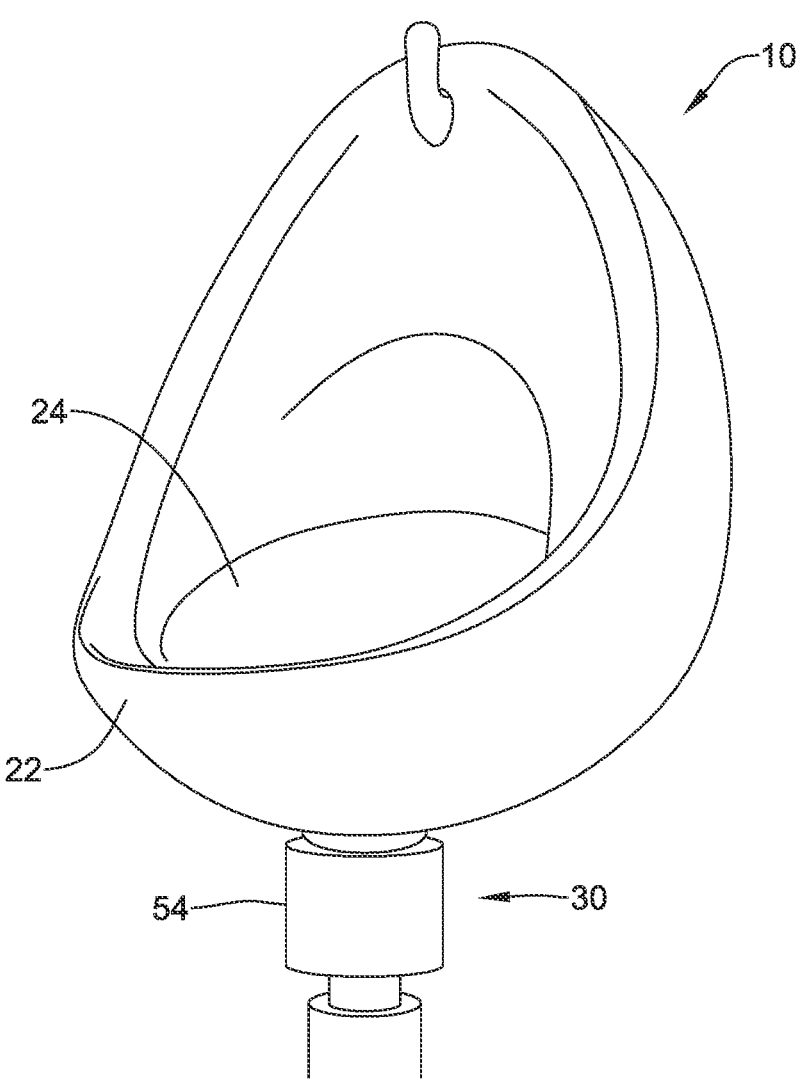
FIG. 7 is a schematic perspective view of a toilet incorporating an illustrative urinalysis system.

FIG. 7 is a schematic perspective view of a toilet 10 in a urinal configuration having the base 22 and the basin 24. When the toilet 10 has a urinal configuration and/or other suitable configurations, the urinalysis system 30 may be implemented in a housing 54 (e.g., wherein the housing may form part of a drain pipe) that may be a portion of the toilet's drain line and/or retrofitted to the toilet drain line. In some cases, the urinalysis system 30 may be configured to passively collect a urine sample for testing without requiring aim by the subject.

Figure 8:
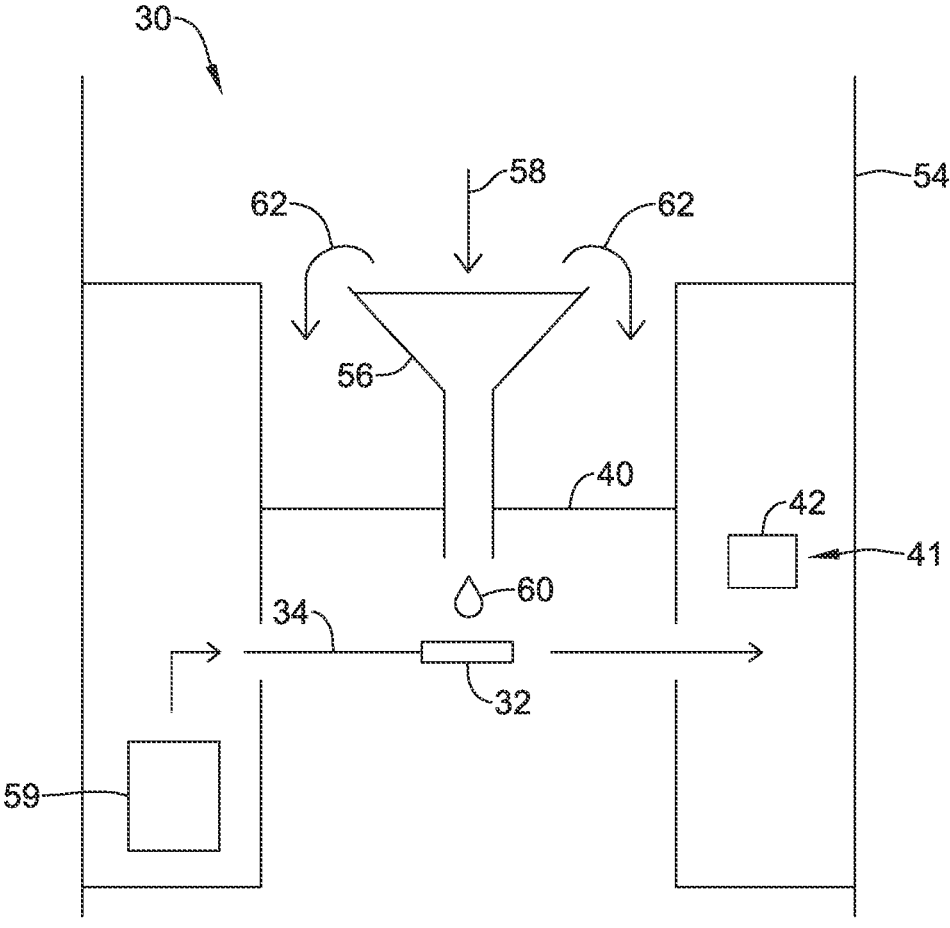
FIG. 8 is a schematic diagram of an illustrative urinalysis system.

FIG. 8 is a schematic cross-sectional diagram of the urinalysis system 30 at least partially integrated into the housing 54. Although the urinalysis system 30 depicted in FIG. 8 is in the housing 54 of the toilet 10 in a urinal configuration, the urinalysis system 30 depicted in FIG. 8 (and described in further detail below) may be implemented in a sit-down toilet and/or other suitable toilet system. In some cases, the configuration of the urinalysis system 30 of FIG. 8 may be considered a passive collection urinalysis system because it collects a desired amount of urine for sampling without action by the subject.

In the urinalysis system 30 depicted in FIG. 8, urine may flow from the basin 24 of the toilet 10 into a sample collection unit 56 in a direction of arrow 58. In some cases, the sample collection unit 56 may have a funnel configuration, but other configurations are contemplated. Prior to and/or during a subject providing a sample (e.g., urine) (e.g., in response to a signal indicating an incoming subject, a presence of a subject, and/or a presence of urine), the test material holder 34 may obtain test material 32 from a cartridge 59 storing test material and position the test material at an outlet of the sample collection unit 56, as depicted in FIG. 8. In some cases, a conveyor may be utilized for moving test material 32 from the cartridge 59 to the test material holder 34.

The sample collection unit 56 may be sized and/or shaped to deliver a desired volume of sample 60 (e.g., urine) to the test material 32 supported by the test material holder 34. In the configuration of the urinalysis system depicted in FIG. 8, the sample collection unit 56 may be configured such that excess sample overflows the sample collection unit 56 (e.g., in the direction of arrows 62), passes down the toilet drain line, and avoids further contact with the test material 32. Additionally or alternatively, other suitable techniques and/or configurations are contemplated for supplying a desired amount of the sample 60 to the test material 32 and disposing of excess sample.

In some cases, the temperature sensing device 40 (e.g., a thermocouple and/or other suitable temperature sensing device) may extend to and or through the sample collection unit 56 to facilitate measuring a temperature of the sample received. Other suitable configurations of the temperature sensing device 40 are contemplated.

The test material 32 may be exposed to the sample 60 for a duration of volume the funnel collects (e.g., as determined for a desired urine exposure time). Once the test material 32 has been exposed to the sample 60 for the desired time/volume, the test material 32 may be passed to the analyzer 41. In some cases, one or more cameras 42 may be utilized for capturing images of the test material for colorimetric analysis and/or other suitable analyses. Images and/or results of analyses of the sample 60 (e.g., temperature) and/or the test material 32 exposed to the sample 60 may be stored in one or more local and/or remote databases. Additionally and/or alternatively, the images and/or results of analyses of the test material 32 exposed to the sample 60 may be outputted via a wired or wireless connection to one or more remote servers and/or mobile devices.

Drugs of abuse are widely tested for in a variety of environments (e.g., sports, jails, abuse/addiction treatment programs, etc.). Often cups may be used to collect urine from a subject while a third party (e.g., a guard, professional sample tester, etc.) witness collection of the urine in the cup. For the purpose of detecting a presence of drugs of abuse, the cups may be configured to react to urine samples after being exposed to urine for a specified period of time. Too short of an exposure time may result in a test that lacks sensitivity, for example. Too long of an exposure time and the test may result in false-positives, for example. Once the cup has been exposed to urine for the specified period of time, the third party may observe the results of the test and document the findings using paper records and/or a secure computer system. This manual, laborious process may preclude the use of this type of testing as often as desired and/or preferred (e.g., in order to keep sports clean, provide safety to people, keep facilities safe, etc.).

To facilitate testing for drugs of abuse and/or other suitable drugs or metabolites in a controlled environment and on a regular basis, the toilet 10 may be configured to collect and/or analyze samples in a secured manner. In some cases, the toilet 10, as depicted in FIG. 9, may be a urinal configuration, but this is not required, and may be configured to accept already existing drug testing cups (e.g., cups that react to urine samples after exposure for a predetermined period of time) to offer a complete drug test solution that may be automated and provides documentation of the subject, the test process, and/or the test results.

Figure 9:
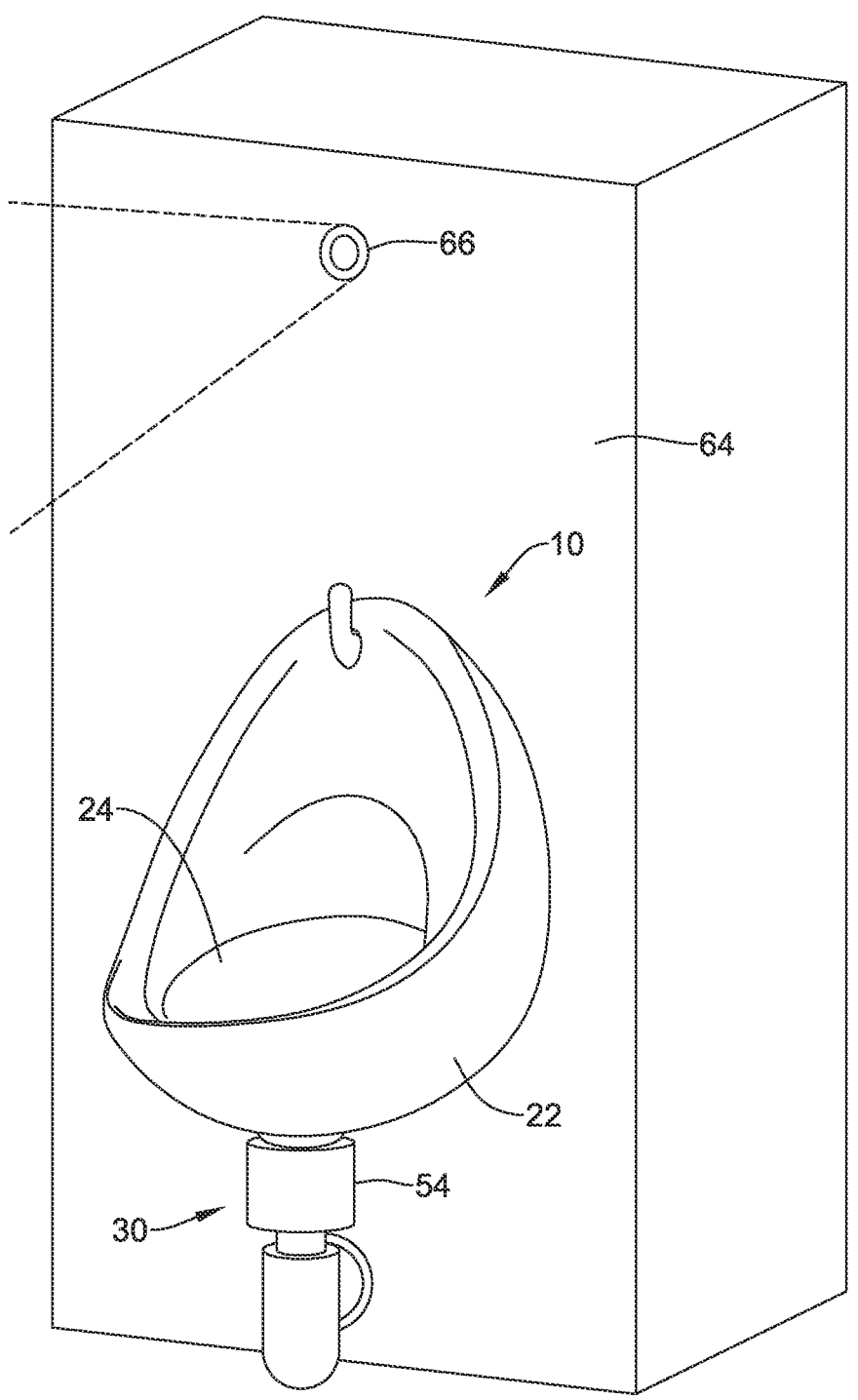
FIG. 9 is a schematic perspective view of a toilet mounted on a wall and incorporating an illustrative urinalysis system.

FIG. 9 depicts the toilet 10 in a urinal configuration secured to a wall 64, where the toilet includes the urinalysis system 30 at least partially within the housing 54 and configured to provide secure sample testing. The urinalysis system 30 used with the toilet 10 of FIG. 9 may include a similar passive sample collection system as discussed above with respect to FIG. 8. For example, a predetermined amount of sample may be passively collected and provided to test material (e.g., a test cup). Further a cup conveying system may be incorporated into the toilet 10 and/or the urinalysis system 30 at or below the housing 54 and/or at one or more other suitable locations.

As depicted in FIG. 9, one or more subject identification cameras 66 may be provided for use in identifying a subject that is to provide or is providing a sample for testing. In some cases, the one or more cameras and/or associated controllers may be configured to recognize a face, a height, and/or one or more other suitable physical characteristics of the subject.

Figure 10:
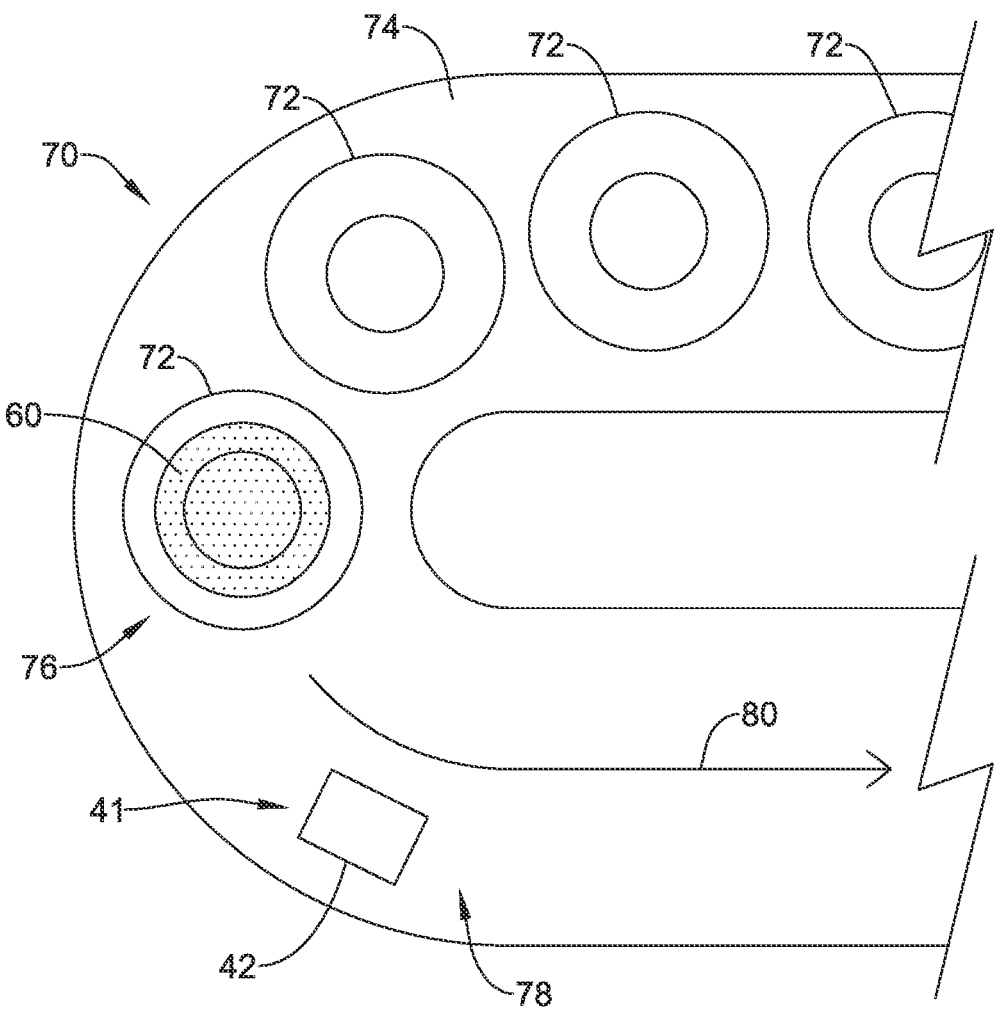
FIG. 10 is a schematic top view of a portion of an illustrative urinalysis system.

FIG. 10 depicts a cup conveying system 70 in which cups 72 (e.g., standard drug test cups) may be conveyed along a conveyor 74 (e.g., a portion of a test material holder) from a cup storage area (not shown) to a sample receiving area 76 to an analysis area 78 and to a storage area (not shown) in the direction of arrow 80. Once the cup receives the sample 60 at the sample receiving area 76, the cup 72 containing the sample 60 may advance to analysis area 78 at which the one or more cameras 42 of the analyzer 41 may capture images of the cup 72 and/or the sample 60. Additionally or alternatively, the analyzer 41 may analyze the sample 60 in one or more other suitable manners.

Once the cup 72 and the sample 60 arrive at the analysis area 78, the analyzer 41 may be configured to capture an image of cup 72 and sample 60 from which a sample amount (e.g., urine level) may be determined. Further, after an incubation period (e.g., a predetermined amount of time, such as 5-10 minutes in one example), the analyzer 41 may capture further images that facilitate determining the results of the sample test (e.g., how the testing cup reacted to the sample 60). In some cases, the results of the test, which may include one or more captured images, may be printed on the cup 72 with the sample 60 via a printer in-line with the conveyor 74. Further, the subject's name, one or more images taken by the one or more subject identification cameras 66, a time of the test, an incubation period, date of the test, location of the test, and/or other suitable data may be printed on the cup. After printing, if any, the cup 72 may be conveyed to a refrigerator storage area in or behind the wall 64 and/or at one or more other suitable locations.

A digital record of the test that includes all of the data printed on the cup 72 and/or additional or alternative data may be stored in one or more database. In some cases, the digital record may be stored at the urinalysis system 30 and/or at a remote server. The digital record may be provided to a mobile device of the subject and/or the remote server through one or more wired and/or wireless connections.

In some cases, the sample test material 32 (e.g., a test strip, a cup with a sample therein, etc.) may be sent to a lab for mass spectrometric follow-up testing and analysis. In one example, if a sample is indicated as including a drug or metabolite for which a test is performed (e.g., a positive test result), the test material and/or sample may be sent to a lab for mass spectrometric follow-up. As such, the test material and/or sample may be provided to a refrigerated storage area for shipment to a mass spectrometry testing facility. Additionally or alternatively, mass spectrometer test equipment may be incorporated into the urinalysis system 30 and/or may be in communication with the urinalysis system 30 and the follow-up mass spectrometry testing may be performed automatically when a predetermined drug or metabolite for which a test is performed is found to be in the test sample.

Figure 11:
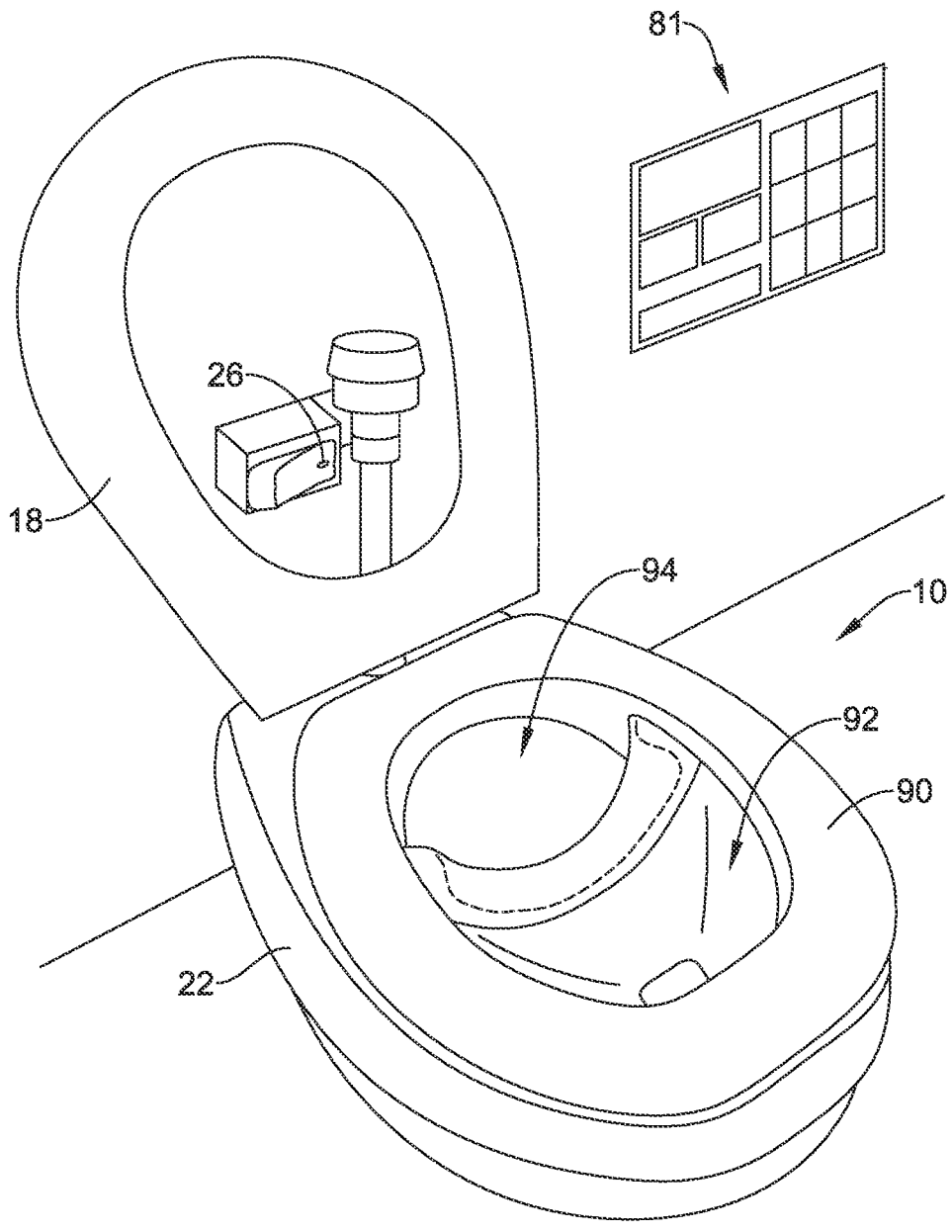
FIG. 11 is a schematic perspective view of a toilet incorporating an illustrative urinalysis system.
Figure 12:
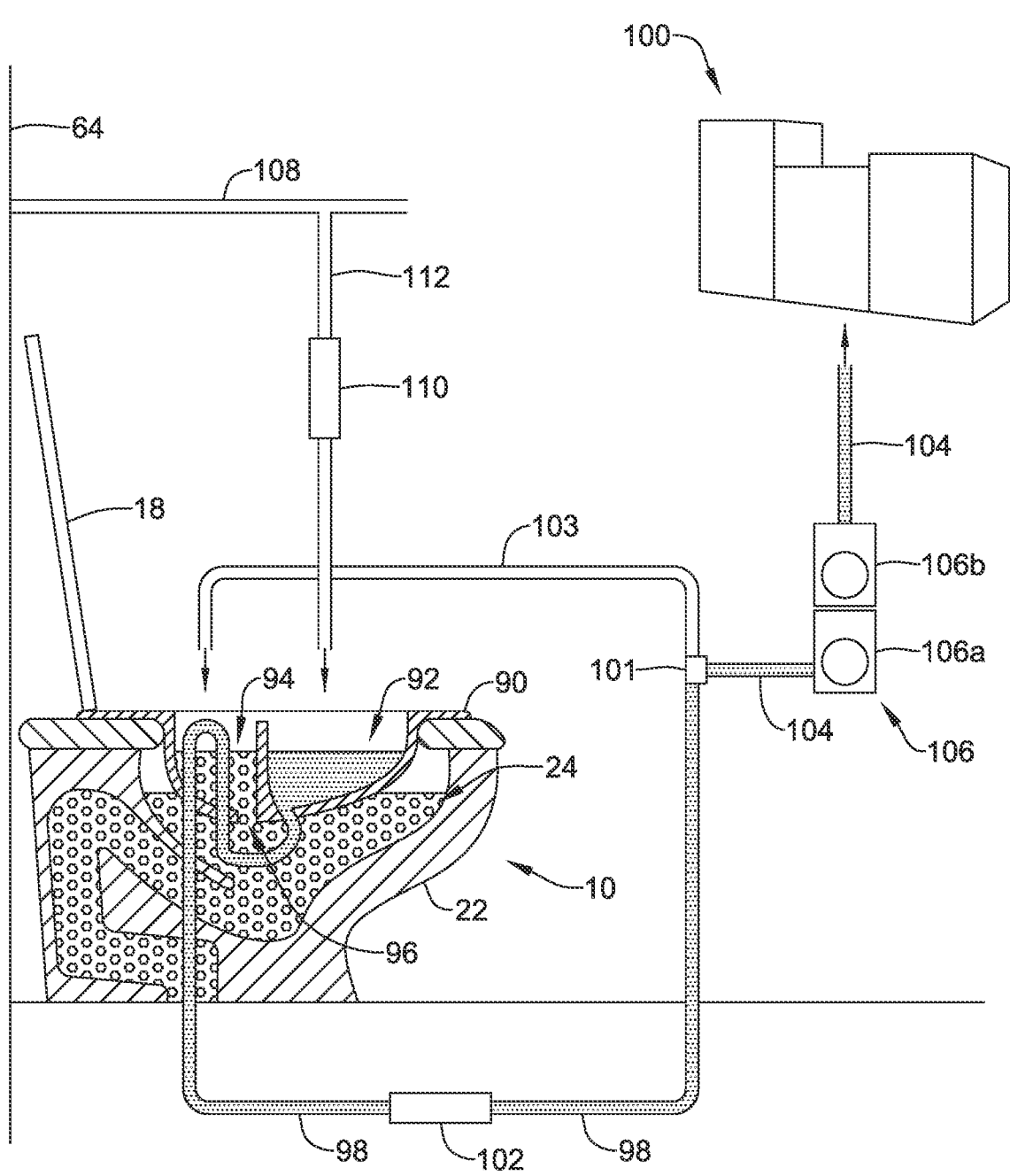
FIG. 12 is a schematic diagram of the toilet incorporating the illustrative urinalysis system, as depicted in FIG. 11.

FIGS. 11 and 12 depict a toilet 10 configured for use in performing urinalysis testing on a sample (e.g., urine) received from a subject using a urinalysis system 30 configured for mass spectrometry testing. Although the example urinalysis system 30 of FIGS. 11 and 12 is depicted in a sit-down toilet configuration, the urinalysis system 30 configured for mass spectrometry testing may be implemented in a urinal and/or other suitable toilet system configuration.

In some cases, the toilet 10 in FIGS. 11 and 12 may be configured as a smart toilet with a user interface 81, which may include a display with selectable options (e.g., a touch screen and/or selectable buttons, see e.g., FIG. 18) in communication with a controller (e.g., similar to or different than the controller 48) for controlling operation of the smart toilet and testing of urine samples. In some cases, the user interface 81 may indicate a toilet is available for use, provide a key pad to enter a subject identification code, a selectable flush button, one or more biometric sensors, etc.

Although a controller is not shown with respect to the systems depicted in FIGS. 11 and 12, it is contemplated that a controller including one or more processors and memory, along with I/O ports, similar to or different than the controller 48 discussed above may be utilized with the toilet 10 and associated system for urinalysis testing. In some cases, the systems depicted in FIGS. 11 and 12 may combine to be a smart system controlled by the controller through the user interface 81 and/or one or more other suitable user interfaces.

The toilet 10 may include the seat 18, the base 22, which may at least partially define the basin 24 (see FIG. 12), and an automatic flusher 26. In some cases, to facilitate mass spectrometer urinalysis testing of a received sample, a sample collector 90 (e.g., an insert and/or divider) may be part of the base 22, may be placed on the base 22, and/or may be at least partially within the basin 24. As depicted in FIG. 11, the sample collector 90 may include and/or divide the basin 24 into at least a sample collection portion 92 (e.g., a sample reservoir) that keeps a sample separated from toilet water and a flush portion 94 that is exposed to toilet water and allows for defecation and/or use of toilet paper. Once a subject has used the toilet 10 (e.g., provided a urine sample in the sample collection portion 92 and/or otherwise used the toilet 10), the subject may flush the toilet by selecting a user number (e.g., "Subject 5"), entering a user identification (ID) code (e.g., a personal identification number (PIN), etc.), etc. and selecting a flush button via the user interface 81. If the subject is automatically identified (e.g., via biometric sensor), the subject may not be required to enter an identification may select a flush button and/or the system may automatically flush after a sample has been received. Once a flush process has been selected or otherwise initiated, the rest of the process may be at least partially or fully automated and the subject may walk away.

FIG. 12 depicts a schematic diagram showing a cross-section of the toilet 10 with the sample collector 90 of FIG. 11, along with a system flow for performing mass spectrometry on a received sample. In some cases, the flush portion 94 of the sample collector 90 may be exposed to regular toilet water (e.g., represented by hexagonal shapes in FIG. 12) of the toilet 10 and may have an opening 96 to the basin 24 such that a user may be able to use the toilet in a standard manner.

The sample collection portion 92 of the collector 90 may be in communication with sample tubing 98 through which a sample (e.g., represented by dots in FIG. 12) collected in the sample collection portion 92 may travel for analysis by a liquid chromatography mass spectrometry (LCMS) unit 100 and/or other suitable mass spectrometry or analysis unit. Although a particular configuration for the sample tubing 98 is depicted in FIG. 12, the sample tubing 98 may take on one or more other suitable configurations. Further, a temperature sensor (e.g., thermocouple, thermometer, etc.) may be in communication with the sample collection portion 92 and/or exposable to fluid in the sample collection portion 92 to sense one or more parameters related to a temperature of sample urine and output the one or more parameters sensed to a controller of the urinalysis system 30. The temperature of the sample urine may be used as a proxy for body temperature, but this is not required.

In some cases, a sample pump 102 may be utilized to pump a sample received in the sample collection portion 92 of the sample collector 90 to the LCMS unit 100 and/or to the flush portion 94. In one example, in response to a user selecting to flush the toilet, the sample pump 102 may be initiated to pump the sample urine from the sample collection portion 92 along a sample flow path.

In some cases, an interface 101 (e.g., a T-interface and/or other suitable interface) may be utilized to split the sample tubing 98 between a flush tubing 103 that sends a received sample to the flush portion 94 of the sample collector 90 for flushing and a testing tubing 104 that sends a received sample to the LCMS unit 100 for testing. The sample tubing

98, the interface 101, the flush tubing 103, and the testing tubing 104 may entirely or at least partially form the sample flow path.

Sample urine may be detected along the sample tubing 98 at one or more locations. In some cases, one or more liquid sensors may be placed along the sample tubing 98 at one or more locations to sense and/or detect an amount of fluid in the sample tubing 98. The liquid sensors may be any suitable type of liquid sensing device including, but not limited to, ultrasonic liquid sensors.

In one example configuration, a liquid sensor may be placed at or adjacent to the interface 101. Once a urine sample has been detected at or adjacent to the interface 101, the sample pump 102 may stop pumping the sample urine through the sample tubing 98 and the LCMS unit 100 may begin a process of obtaining a specimen for testing and analysis from the received urine sample.

The process of the LCMS unit 100 may include automatically suctioning a predetermined amount of the urine sample to be used as the specimen into a sample loop of one or more valves 106 (e.g., a first valve 106a and a second valve 106b). The suction may be performed automatically using a syringe of the LCMS unit 100 and/or performed in one or more other suitable manners. Once the specimen is obtained in the sample loop, the LCMS unit 100 may perform its testing and analysis of the sample urine in the specimen and toilet system may begin the process of cleaning its components and measuring a total volume of the urine sample received in the sample collection portion 92.

Using the liquid sensors, a pumping rate of the sample pump 102, and a total pumping time, a total volume of the urine sample may be determined. Such measurements may be useful measures of hydration of the subject providing the urine sample.

In some cases, the toilet 10 may include and/or may be in communication with a plumbing line 108 from which a cleaning pump 110 may pump water to a cleaning tube 112 in communication with the sample collection portion 92 of the sample collector 90. In some cases, the cleaning pump 110 may be configured to pump water in response to a flush request via the user interface 81, after a predetermined time (e.g., a predetermined time after starting testing process, etc.), and/or in response to one or more other signals.

To facilitate cleaning the components of the system, the urine sample remaining in the sample tubing 98 and the sample collection portion 92 may be pumped to the flush tubing 103 and emptied into the flush portion 94. Simultaneously or subsequently, the sample collection portion 92, the sample tubing 98, the interface 101, the flush tubing 13, the testing tubing 104, the valves 106, and/or other components of the sample flow path may be flushed with fluid (e.g., clean water) pumped into the sample collection portion 92 from the plumbing line 108 to the cleaning tube 112 using the cleaning pump 110.

The flushing with fluid may occur one or more times. In some cases, a cleaning solution followed by a final rinse may be used to further clean the sample flow path. The cleaning solution may include ammonia, alcohol, and/or one or more other suitable cleaning compounds. After cleaning is complete, the system may cause the toilet to be flushed to ensure nothing remains in the toilet after cleaning. The total run time of obtaining a sample, testing and analyzing the sample, and cleaning the system may be thirty (30) minutes or less, twenty (20) minutes or less, and/or one or more other suitable amounts of time. In one example, the total run time for one process iteration is less than twenty (20) minutes.

Figure 13:
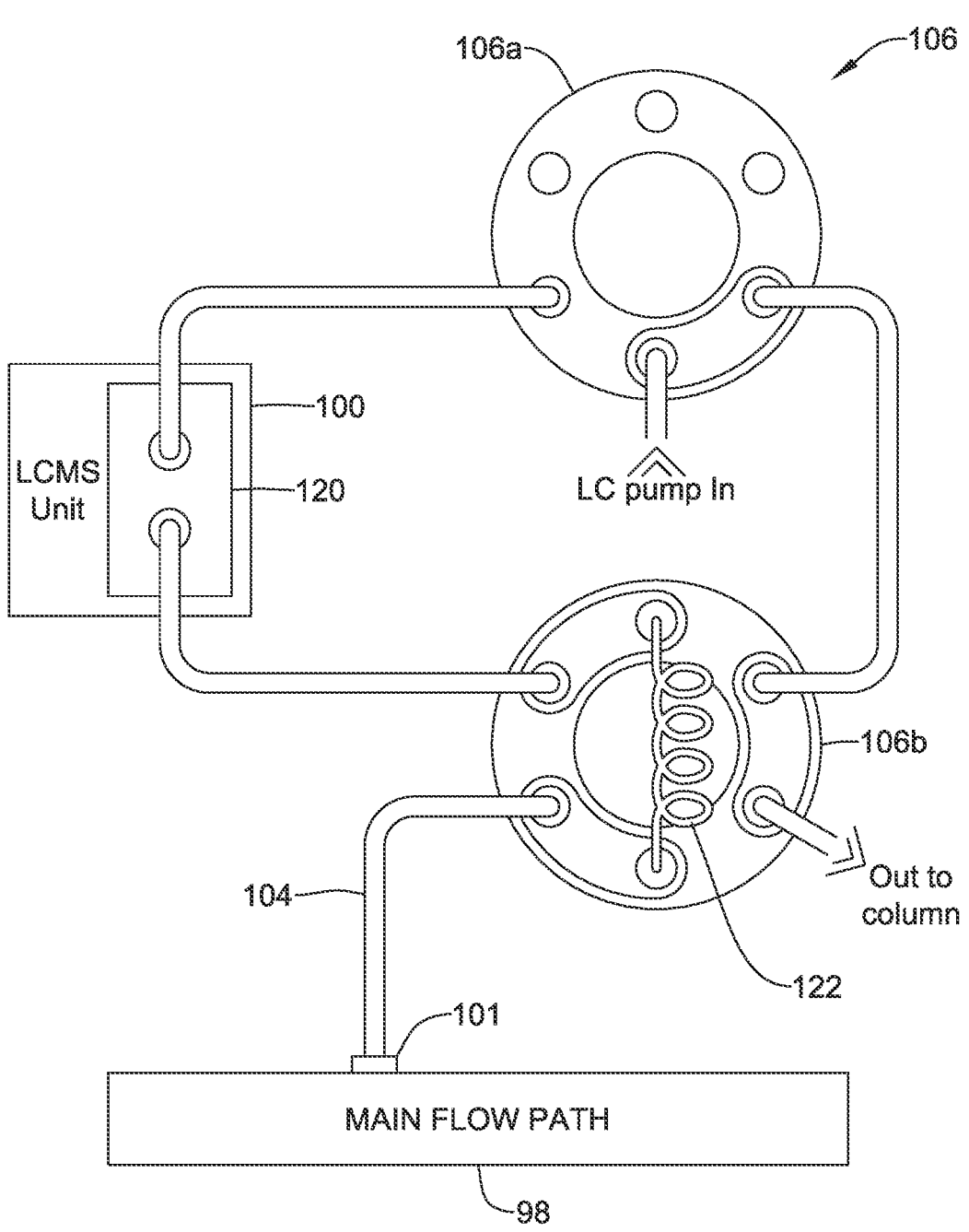
FIG. 13 is a schematic diagram of an illustrative valve system for a urinalysis system, the illustrative valve system is in a first position.
Figure 14:
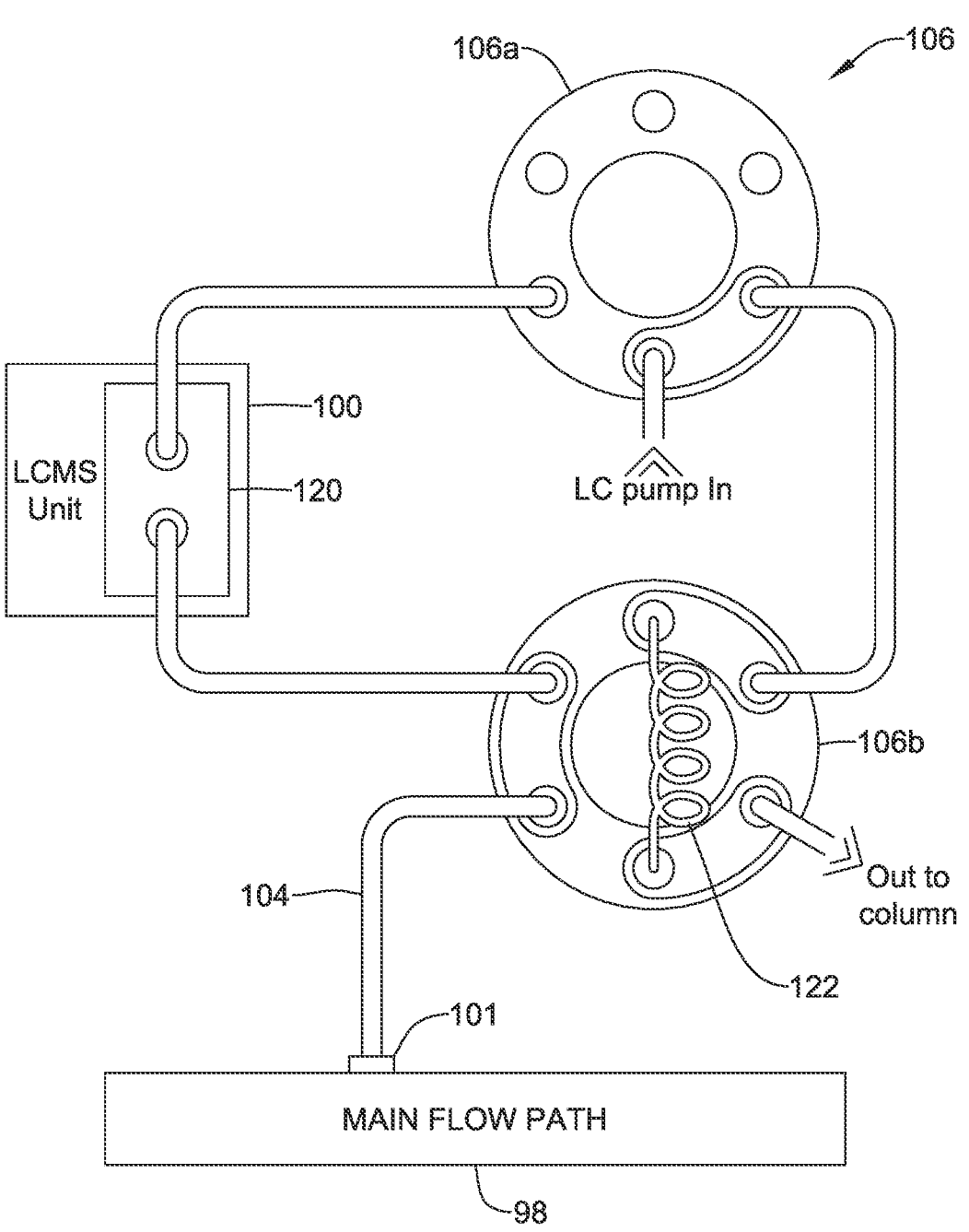
FIG. 14 is a schematic diagram of an illustrative valve system for a urinalysis system, as depicted in FIG. 13, the illustrative valve system is in a second position.

FIGS. 13 and 14 depict valves 106 (e.g., the first valve 106*a* and the second valve 106*b*) that may be utilized to direct a sample through the testing tubing 104 to the LCMS unit 100. In one example, the first valve 106*a* and the second valve 106*b* may be external 6-port, 2-position valves, but this is not required and other valve configurations are contemplated. FIG. 13 is a schematic depiction of the first valve 106*a* and the second valve 106*b* in a first position (e.g., a fill position). FIG. 14 is a schematic depiction of the first valve 106*a* and the second valve 106*b* in a second position (e.g., a dispense position).

FIG. 13 depicts the valves 106 in a first position in which a syringe plunger 120 (e.g., schematically depicted as a box) of the LCMS unit 100 is in communication with a sample loop 122. As discussed above, in response to a liquid sensor sensing fluid at or adjacent the interface 101, the syringe plunger 120 of the LCMS unit 100 may automatically suction a specimen of sample urine into the sample loop 122. Once the sample loop 122 is filled, one or both of the valves 106 may move or switch (e.g., automatically and/or in response to a manually initiated signal).

FIG. 14 depicts the second valve 106*b* in a second position in which the syringe plunger 120 is separated from the sample loop 122. However, when the second valve 106*b* is in the second position, the sample loop 122 is in communication with an output to the LCMS unit 100 and the specimen in the sample loop 122 (e.g., a predetermined amount of the urine sample suctioned into the sample loop when the valves 106 are positioned as depicted in FIG. 13) may be provided to the LCMS unit 100 for testing and analysis.

The user interface 81 may be any suitable user interface in communication with a controller (e.g., the controller 48 and/or one or more other suitable controller) that permits the controller to display and/or solicit information, as well as accept one or more user interactions with the controller. For example, the user interface 81 may permit a subject to enter a PIN, enter a message, select options, listen for spoken words through a microphone, play sounds through a speaker, and the like. In some cases, the user interface 81 may include a display and a distinct keypad, but this is not required and the keypad may be part of the display. A display may be any suitable display. In some instances, the display may include or may be a liquid crystal display (LCD), a light emitting diode display (LED), etc. In some cases, the display may be a fixed segment display or a dot matrix display (e.g., a dot matrix LCD display). If desired, the user interface 81 may be or may include a touch screen (e.g., a touch screen LCD panel, etc.) that functions as both a display and a keypad. In some cases, the user interface 81 may optionally include memory. In some cases, the user interface 81 may include one or more electromechanical input devices (e.g., a switch, a push button, etc.) for use in operating the toilet systems discussed herein (e.g., toilets 10 and/or urinalysis systems 30).

Figure 15:
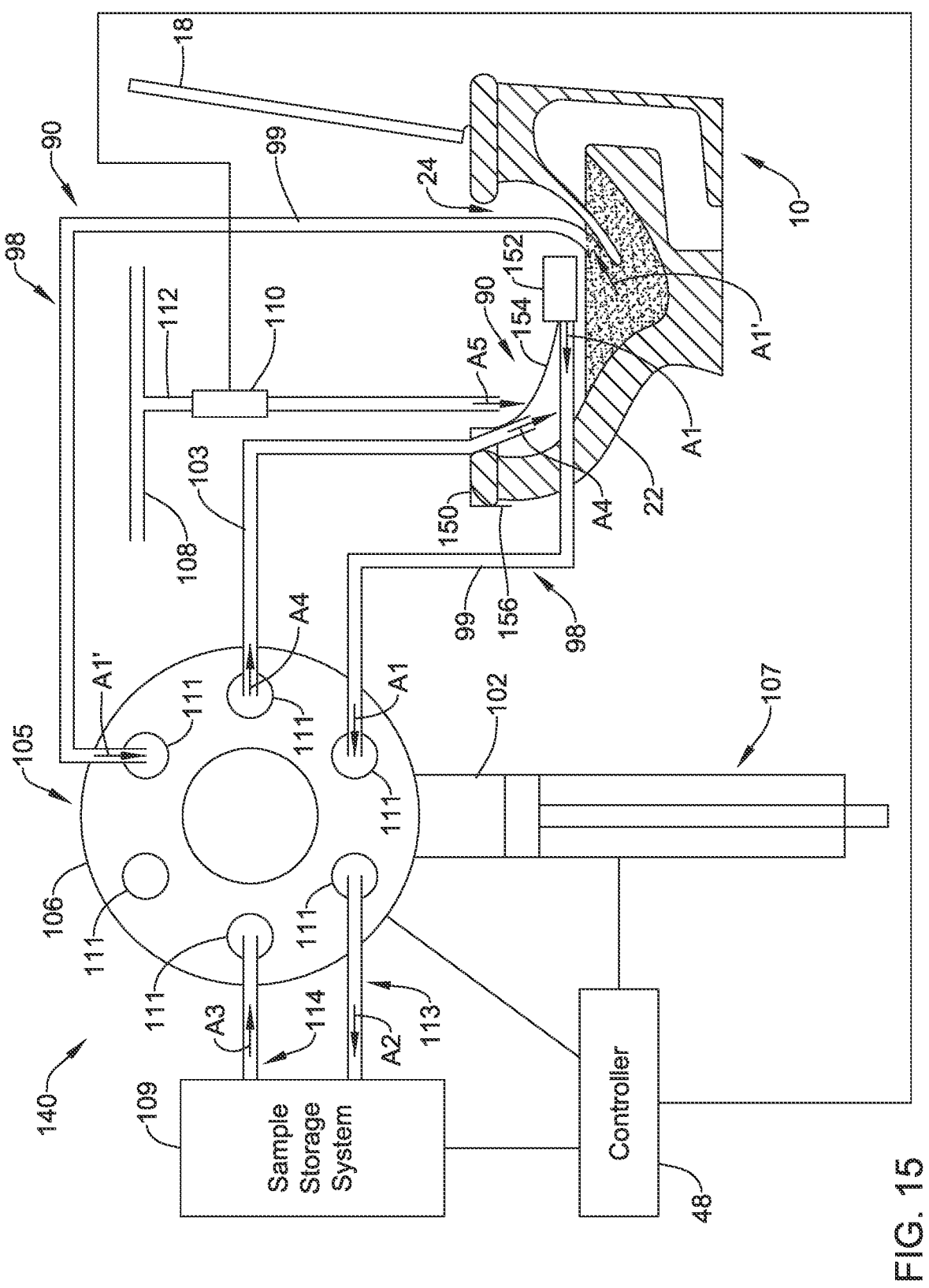
FIG. 15 is a schematic diagram of a sample collection system.

FIG. 15 schematically depicts an illustrative sample collection system 140 configured to be in use with the toilet 10 to collect urine samples. The sample collection system 140 may collect pure urine samples and/or samples that are a mix of urine and toilet water. Although the example sample collection system 140 of FIG. 15 is depicted in conjunction with the toilet 10 having a sit-down configuration, the sample collection system 140 may be implemented in or with a urinal and/or other suitable toilet configuration.

The toilet 10 as depicted in FIG. 15 may include the seat 18 and the base 22, which may at least partially define the basin 24 (e.g., with fluid therein as depicted by the shaded portion in the basin 24), similar to as discussed in further detail above. The sample collection system 140 may include a configuration of the sample collector 90, which may be at least partially positionable within the toilet 10. For example, the sample collector 90 may be part of the base 22, may be placed on and/or secured to the base 22, and/or may otherwise be positioned to be at least partially within the toilet 10. In some cases, the sample collector 90 is releasably attachable to the toilet 10.

The sample collector 90 may have any suitable configuration and one or more sample collectors 90 may be utilized to collect samples for analysis. In one example, two sample collectors 90 may be utilized, where a first sample collector 90 may be utilized to collect samples of urine mixed with toilet water and a second sample collector 90 may be utilized to collect samples of only urine or mostly only urine.

Two example configurations of sample collectors 90 are depicted in FIG. 15. A first configuration of the sample collector 90 depicted in FIG. 15 includes a first sample flow line or sample collecting tubing 99 (e.g., the sample tubing 98 and/or other suitable sample collecting tubing), where a distal end of the sample collecting tubing 99 extends into or is positionable in a basin configured to collect urine (e.g., the basin 24 and/or other suitable basin) and may be considered a sample collection portion 152. A second configuration of the sample collector 90 depicted in FIG. 15 may have a toilet connecting portion and a sample collection portion. For example, the sample collector 90 may have a top connecting portion 150, a sample collection portion 152, a urine direction portion 154 configured to direct urine to the sample collection portion 152, and a side connecting portion 156. Two or more of the top connection portion 150, the urine direction portion 154, and the side connection portion 156 may work together to facilitate securing or connecting the sample collector 90 to the toilet 10. Other suitable configurations of the sample collectors 90 are contemplated.

In some cases, the first configuration of the sample collector 90, the second configuration of the sample collector 90, and/or one or more other suitable configurations of the sample collector 90 (e.g., as discussed herein or otherwise) may be utilized together and/or independently to collect samples including urine content. In one example, the first configuration of the sample collector 90 may be in communication with the second configuration of the sample collector 90 to facilitate collecting a urine sample and a urine/water mix sample. In another example, only the first configuration of the sample collector 90 may be utilized or only the second configuration of the sample collector 90 may be utilized.

The sample collection portion 152 may have any suitable configuration that facilitates collecting a sample (e.g., sample urine, sample urine/water mix, etc.). In one example, the sample collection portion 152 may be a reservoir having any suitable size configured to collect a sample of sufficient volume for analyses (e.g., analyses as discussed herein). Illustratively, the sample collection portion 152 forming a reservoir may be configured to collect and/or hold three (3) milliliters of fluid and/or other suitable amounts of fluid. Another example configuration of the sample collection portion 152 may be an open portion of a tube that extends into fluid (e.g., urine, a mix of urine and water, etc.) that can be sampled for analysis (e.g., as depicted in FIG. 15 with the first configuration of the sample collector 90). Other suitable configurations of the sample collection portions 152 are contemplated.

Further, one or more sensors or sensing components may be positioned in or with respect to the sample collector(s) 90.

For example, similar to as discussed above, a temperature sensor may be positioned in or adjacent to the sample collection portion 152 of the sample collector(s) 90 and may be configured to sense measures related to a temperature of sample in the sample collection portions 152. Additional or alternative sensors include, but are not limited to, volume sensors, flow sensors, weight sensors, and/or other suitable sensors. Any suitable number of sensors may be utilized.

The sample collector(s) 90 may feed and/or facilitate feeding sample fluid to a valve system 105, where the valve system 105 may be in communication with a pumping system 107 and a sample storage system 109. A second sample flow line or second sample collection tubing 99 of or in communication with the second configuration of the sample collector 90 is depicted in FIG. 15 and is configured to transfer or facilitate a transfer of sample fluid to the valve system 105. In one example, the sample collection tubing 99 may be a two hundred seventy (270) microliter tubing, but this is not required and other sized tubing is contemplated.

The valve system 105 may utilize one or more valves 106. As depicted in FIG. 15, the valve system 105 may utilize a single valve 106, where the single valve 106 has six (6) ports 111 and any two of the ports 111 may be put into communication with one another to form an input port and an output port. Additionally or alternatively, the valve 106 may be configured to have a first port connected to a pump of the pump system 107 and cause one or more of the other ports to be in selective communication with the pump. Other suitable valve configurations are contemplated, including, but not limited to, other configurations discussed herein. The valve system 105 may be controlled by electronics therein and independent of or in conjunction with other systems of the sample collection system 140.

In one example valve system 105, as depicted in FIG. 15, the valve 106 may be configured such that the sample pump(s) 102 (e.g., a syringe pump as depicted in FIG. 15) of the pumping system 107 may be connected to the valve 106 and the other ports 111 of the valve 106 may be in selective communication with the sample pump 102. In this configuration, a sample may be drawn into the sample pump 102 through one of the sample collecting lines or tubes 98, 99 in the direction of arrows A1 and A1' when the valve is in a first configuration and pushed out of the sample pump 102 and into the storage line or tubing 104 (e.g., a one hundred sixty (160) microliter tubing and/or other sized tubing) in the direction of arrow A2 when the valve is in a second configuration. When the valve 106 is in a third configuration, excess sample or sample waste (e.g., sample overflow and/or other sample waste) may be drawn into the sample pump 102 from the sample storage system 109 through the excess sample tubing or line 114 in the direction of arrow A3 and pushed out of the syringe pump 120 into the flush tubing or line 103 (e.g., a waste fluid line) in the direction arrow A4 to dispose of the sample waste in the toilet 10 when the valve 104 is in a fourth configuration. The flush tubing or line 103 may be in communication with the sample collector 90 to direct the flush or waste fluid around and/or into the toilet 10, but this is not required and the flush tubing or line 103 may empty directly into the toilet 10.

Although the pumping system 107 is depicted in FIG. 15 as having a single sample pump 102, the pumping system 107 may be configured with two or more pumps in communication with the valve system 105, the sample storage system 109, and/or the fluid lines or tubing (e.g., the lines or tubing 98, 99, 103, 104, 114, etc.). Example pump types of the pumping system 107 may include, but are not limited to, syringe pumps, peristaltic pumps, pneumatic pumps, hydraulic pumps, diaphragm pump, piston pumps, and/or one or more of other suitable pump types.

In one example configuration, the pumping system 107 may include a first pump configured to pump or facilitate pumping a sample from the sample collection portion 92 of the sample collector 90 to the sample storage system 109 and a second pump configured to pump a sample from the sample collection portion 92 through the fluid lines or tubing and/or pump fluid from the sample storage system through fluid lines or tubing (e.g., the excess sample tubing or line 114 and/or the flush or waste tubing or line 103). Although not required, the first pump may be a precision pump, such as a syringe pump and/or other suitable precision pump, and the second pump may be a less precise pump than the first pump, such as a peristaltic pump and/or other suitable less precise pump. In one example, the precision pump may facilitate pumping precise amounts of fluid for sample storage and/or the less precise pump may be utilized for priming and/or flushing purposes, but this is not required. When included, the second pump(s) may be connected with one or more of the fluid lines (e.g., the lines or tubing 99, 103, 104, 114, etc.) via T-connectors and/or other suitable connectors to facilitate moving fluid through the sample collection system 140.

Similar to as discussed above with respect to FIG. 12, the toilet 10 may include and/or may be in communication with a plumbing line 108 (e.g., a cleansing fluid line) from which a cleaning pump 110 (e.g., where the cleaning pump 110 may or may not be part of the pumping system 107) may pump water in the direction of arrow A5 and out of a cleaning tube 112 (e.g., a cleansing fluid line) for the purpose of providing cleansing fluid (e.g., water and/or other suitable cleansing fluid) to the sample collection portion 152 of the sample collector 90, other portions of the sample collector 90, and/or suitable portions of the toilet 10. In some cases, the cleaning pump 110 may be configured to pump cleansing fluid in response to a flush request via the user interface 81, after a predetermined time (e.g., a predetermined time after obtaining an adequate sample, etc.), and/or in response to one or more other signals.

Although FIG. 15 schematically depicts the plumbing line 108 and the cleaning tube 112 as floating above the toilet 10, the plumbing line 108 may be in communication (e.g., in fluid communication) with a plumbing system of a building and/or a cleansing fluid system and the cleaning tube 112 may be in communication (e.g., fluid communication) with the sample collector 90 or independent of the sample collector 90. When in communication with the cleansing fluid system, the plumbing line 108 and the cleaning tube 112 may selectively (e.g., in response to one or more control signals from the controller 48, a controller of the cleaning pump 110, and/or in response to one or more other suitable control signals) provide water, a cleaner and/or deodorant, and/or a mix of water and a cleaner and/or deodorant to the toilet 10 and/or the sample collector 90. Further, the cleaning tube 112 may be configured to connect to the sample collector 90 and selectively provide a flow of cleansing fluid to the sample collector 90 to clean the sample collector 90 and/or the toilet 10 between sample collections and/or at one or more other suitable times.

The sample storage system 109 may be configured to receive sample fluid that has been tested and/or is to be tested. The sample storage system 109 may be configured to store one or more samples of fluid. In one example, the sample storage system 109 may be configured to receive fluid and separately store samples in individual compartments and/or vials that may be associated with a particular subject that provided the sample.

The sample storage system 109 may be configured to store any suitable amount or volume of sample fluid. In one example, the sample storage system 109 may be configured to store three-hundred (300) microliters of sample in up to forty-eight separate containers, but this is not required and other volumes and numbers of samples/containers are contemplated.

The sample storage system 109 may be configured to provide temperature control of the stored samples. For example, the sample storage system 109 may be configured to heat and/or cool the samples stored therein to a desired temperature. In some cases, the sample storage system may be configured to store the samples at or approximately at four (4) degrees Celsius.

Although the various systems of the sample collection system 140 may include electronic and control software that operates autonomously and/or in communication with controllers of other systems, the sample collection system 140 may utilize the controller 48. The controller 48 may be in communication with one or more of the valve system 105, the pump system 107, sample storage system 109, the pump 110, and/or other systems or components of the sample collection system 140. When included and so connected, the controller 48 may facilitate coordinated control of one or more of the systems of the sample collection system 140, coordinated control of one or more of the systems of the sample collection system 140 in conjunction with the urinalysis system 30, and/or a single user interface from which a user may control and/or access data of the sample collection system 140.

The electronics and/or software of the individual systems and/or the controller 48 may be configured to store user and/or sample information and provide real-time user and/or sample information to remote computing devices (e.g., mobile devices, servers, etc.) over one or more wired and/or wireless networks. Additionally or alternatively, the electronics and/or software of the individual systems and/or the controller 48 may be configured to provide diagnostic monitoring information over one or more networks to monitor the performance and/or health of the sample collection system 140 and provide information on storage space and/or other metrics related to the sample collection system 140.

One or more of the components and/or systems of the sample collection system 140 may be part of the toilet 10 and/or may be retrofitted to or otherwise applied to the toilet 10, as desired. Although the valve system 105, the pumping system 107, and the sample storage system 109 are depicted as being adjacent the toilet 10, one or more of these systems may be located in the toilet 10, at one or more other locations adjacent the toilet 10, and/or remote from the toilet 10 (e.g., in a wall, across a room, in a room other than the room in which the toilet 10 is located, etc.)

Further, although no analysis system is depicted in FIG. 15, one or more analysis systems may be utilized in conjunction with the sample collection system 140. For example, an analysis or testing system may test a sample prior to the sample going to the sample storage system 109, while the sample is at the sample storage system 109 (e.g., the sample storage system 109 may include analysis capabilities), and/or after the sample has been stored at the sample storage system 109. In one example, the urinalysis system 30 may be utilized in conjunction with the sample collection system 140.

Figure 16A:
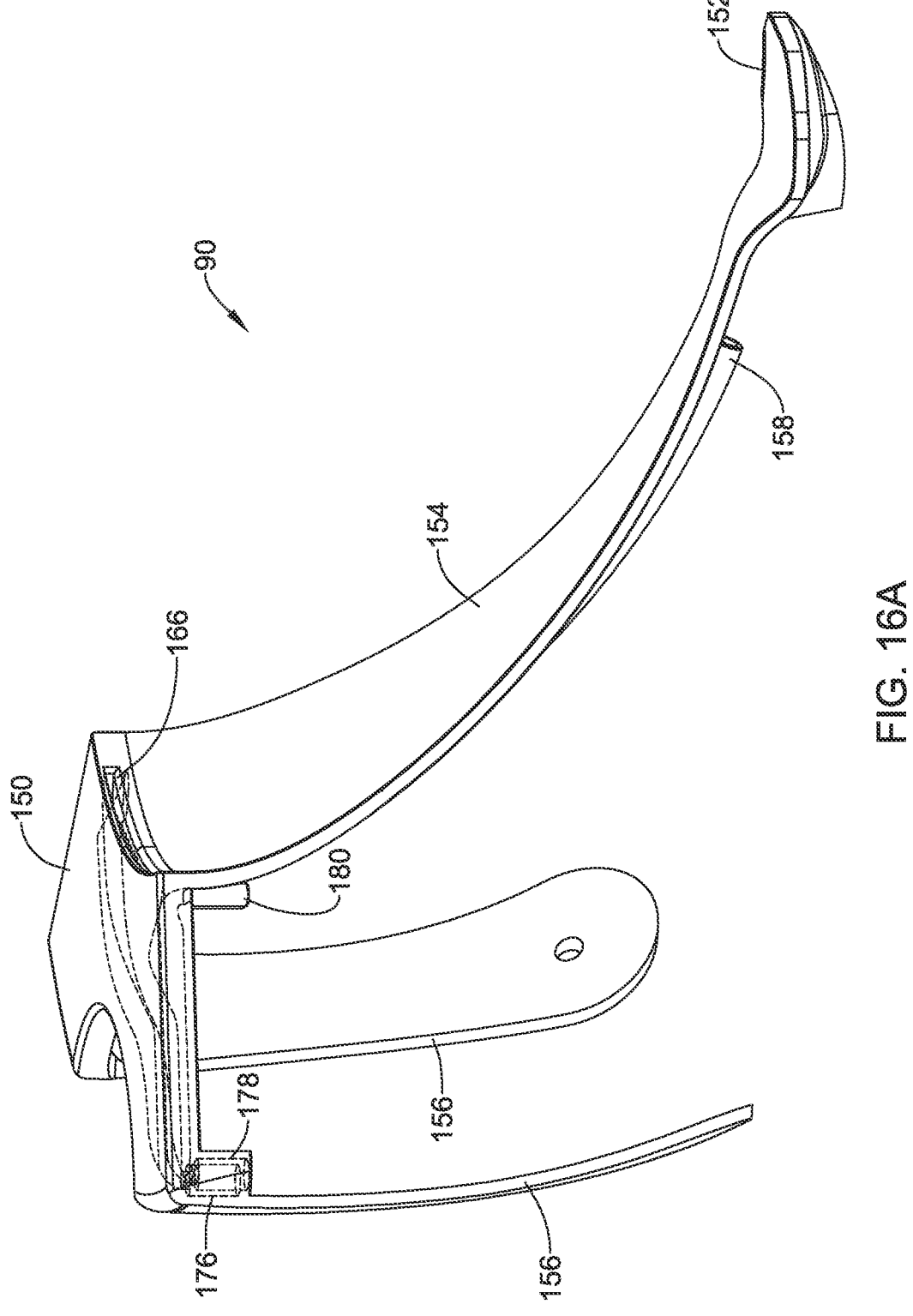
FIGS. 16A-16D are schematic views of an illustrative sample collector.
Figure 16B:
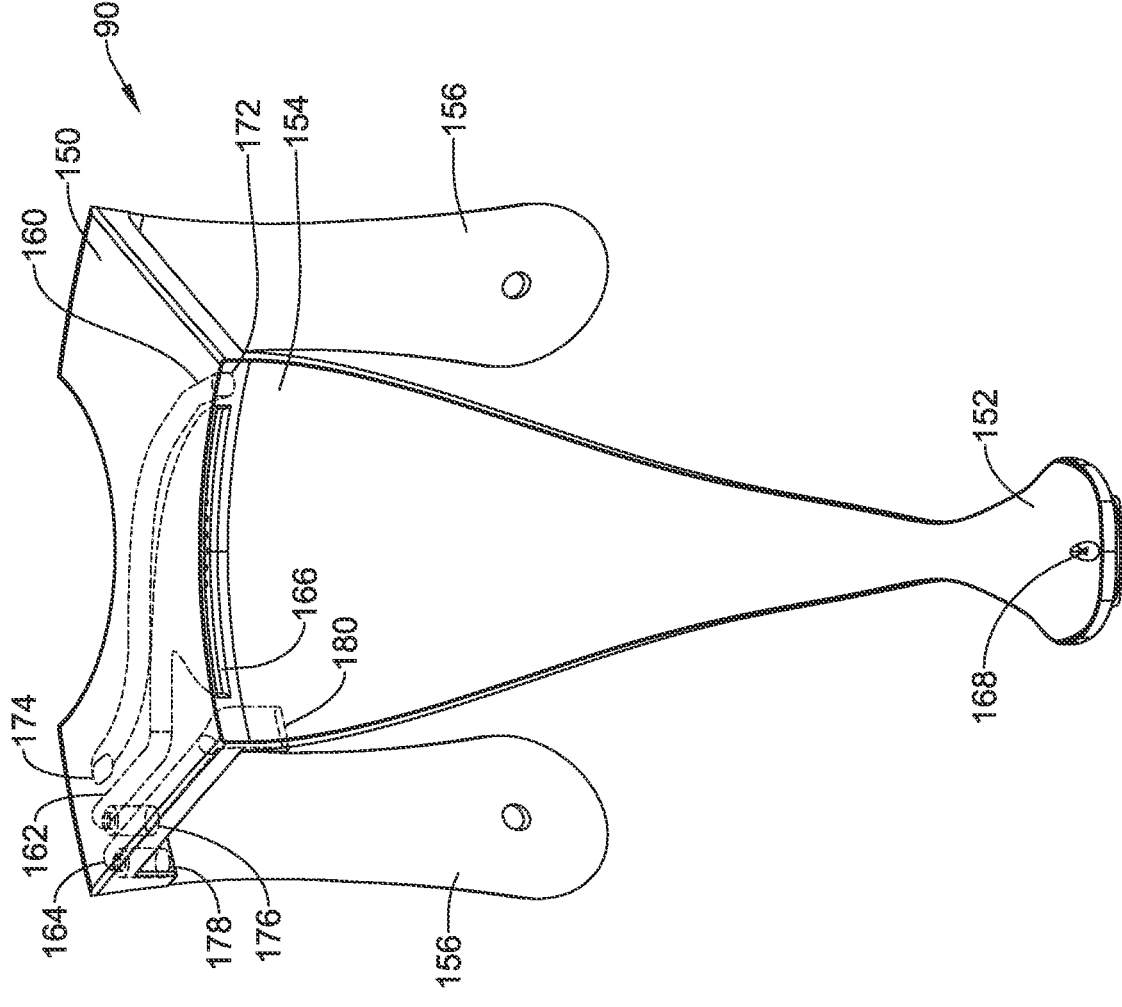
Figure 16C:
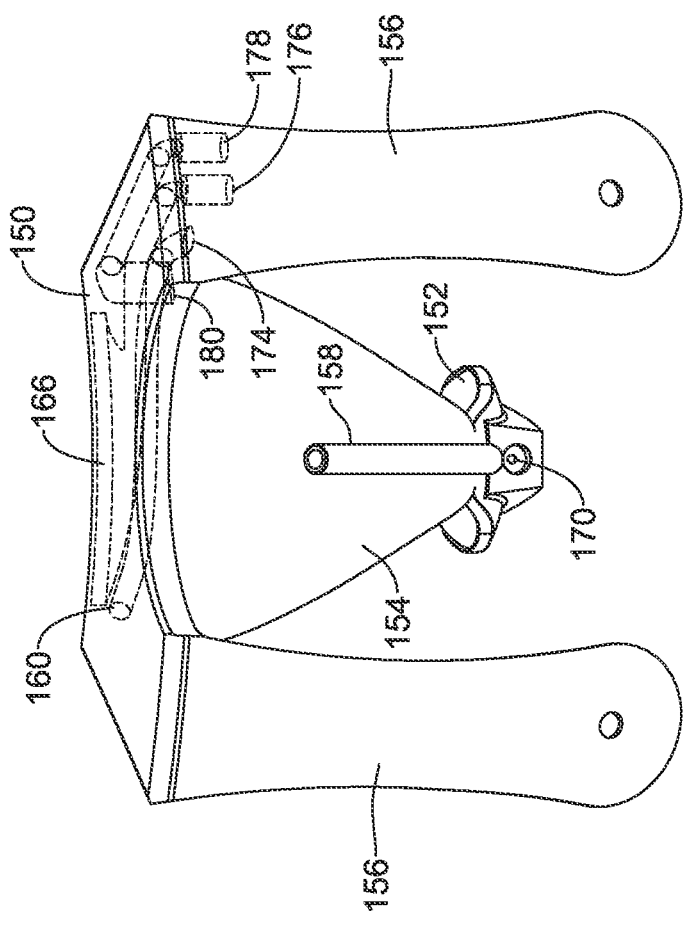
Figure 16D:
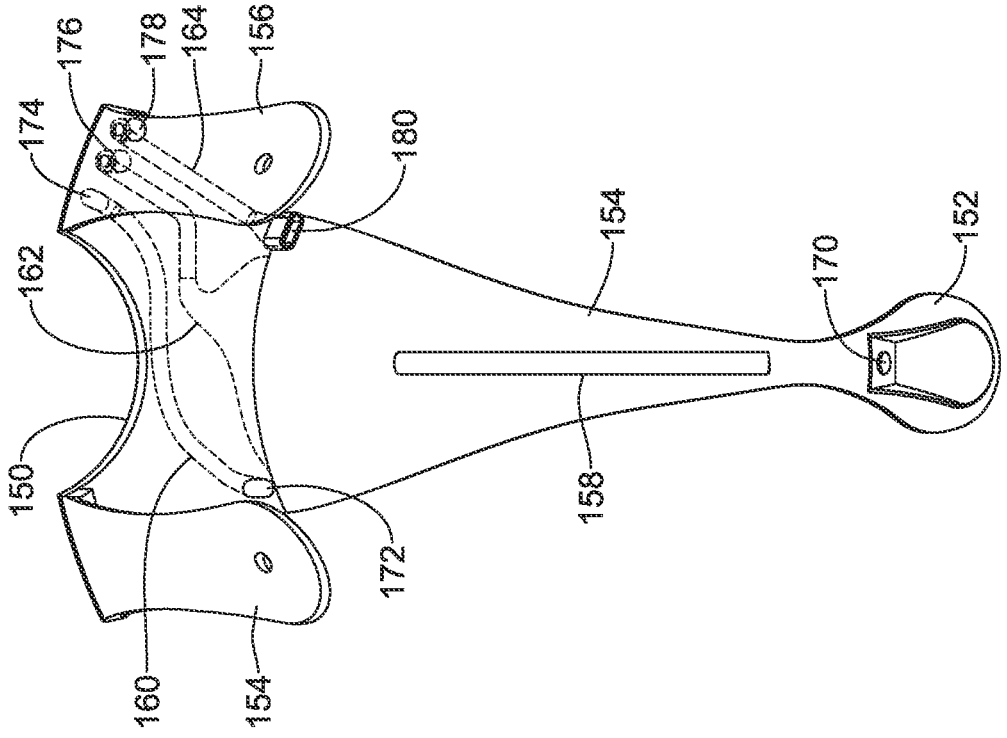

FIGS. 16A-16D depict an illustrative configuration of the sample collector 90 that is discussed herein with respect to FIG. 15. FIG. 16A depicts a side-perspective view of the sample collector 90, FIG. 16B depicts a front-perspective view of the sample collector 90, FIG. 16C depicts a back-perspective view of the sample collector 90, and FIG. 16D depicts a bottom-perspective view of the sample collector 90. Other suitable configurations of the sample collector 90 are contemplated.

As shown in FIG. 16A, the sample collector 90 may include a tube guide 158 configured to facilitate placing a tube (not shown in FIGS. 16A-16D) in communication with the sample collection portion 152 of the sample collector 90. Further, the side connection portion 156 includes two extensions configured to engage an outside of a toilet bowl or base of the toilet 10. The side connection portion 156 may work with the top connecting portion 150 and/or the urine directing portion 154 to connect the sample collector 90 to a rim of the toilet 10 (e.g., similar to as discussed above with respect to the second configuration of the sample collector 90 depicted in FIG. 15, but this is not required).

Using broken lines, FIG. 16B depicts a plurality of flow paths embedded in the top connecting portion 150. A first embedded flow path 160 is configured to be in communication with the sample collecting tubing 98, 99 through which a sample may be collected and transported to the sample storage system 109 and/or a sample analysis system. A second embedded flow path 162 may be or define a cleansing flow path that is configured to be in communication with the plumbing line 108 and/or the cleaning tube or line 112 to receive a cleansing fluid flow (e.g., water, cleaner, a mixture of cleaner and water, etc.) and direct the cleansing fluid flow from the plumbing line 108 and/or the cleaning tube or line 112 to an elongated cleaning fluid output port 166 to the urine direction portion 154 and the sample collection portion 152 to cleanse and/or rinse these portions of the sample collector 90 after a sample has been collected. A third embedded flow path 164 may be or define a waste flow path that is configured to receive waste fluid from the flush line 103 in communication with the valve system 105, pumping system 107, and/or the sample storage system 109, where the third embedded flow path 164 may direct waste fluid around the toilet to ensure the waste fluid is excreted into the basin or bowl of the toilet 10.

Although three embedded flow paths are depicted in the sample collector 90 of FIGS. 16A-16D, fewer than or more than three embedded flow paths may be provided for the purposes discussed herein and/or for other suitable purposes. Further, other suitable configurations of the flow paths are contemplated including, but not limited to, the flow paths not being in embedded in the sample collector 90.

Further FIG. 16B depicts a sample collection port 168 located in the sample collection portion 152 of the sample collector 90. The sample collection port 168 may have any suitable configuration that facilitates drawing fluid from the sample collection portion 152 to sample collecting tubing 98, 99.

FIG. 16C depicts the tube guide 158 extending along a back side of the urine direction portion 154 of the sample collector 90. As can be seen in FIG. 16C, the tube guide 158 may be aligned with a sample collecting tube port 170 to facilitate connecting the sample collecting tubing 98, 99 to the sample collection portion 152 directing the sample the sample collecting tubing 98, 99 away from the sample collector 90 and the toilet 10. Further, the sample collecting tube port 170 on the back side of the sample collecting portion 152 may be in communication with the sample collection port 168 to facilitate drawing fluid from the sample collection portion 152 into the sample collecting tubing 98, 99.

FIG. 16D depicts ports 172, 174 of the first embedded flow path 160 of the sample collector 90. The ports 172, 174 may be configured to connect to one or more segments of the sample collecting tubing 98, 99 that may extend from or through the tube guide 158 and that may extend away from the sample collector 90.

A cleaning fluid input port 176 is depicted in FIG. 16D as being in communication with the second flow path 162 having the cleaning fluid output port 166 (e.g., shown in FIGS. 16A-16C). In some cases, the cleaning tube or line 112 may be connected to and/or be in communication with the second flow path 162 via the cleaning fluid input port 176 and provide cleansing fluid flow to the second flow path 162.

Waste or flush input port 178 and waste or flush output port 180 are depicted in FIG. 16D as being in communication with the third flow path 164. Although not required the waste input port 178 may be positioned on the sample collector 90 so as to connect to the flush tubing or line 103 and receive waste or flush fluid from the flush tubing or line 103 at a location outside of a toilet bowl (e.g., the basin 24) and the waste output port 180 may be positioned on the sample collector 90 so as to output waste or flush fluid from the flush tubing or line 103 and the third flow path 164 at a location inside of the toilet bowl when the sample collector 90 is secured to a toilet (e.g., the toilet 10).

Figure 17:
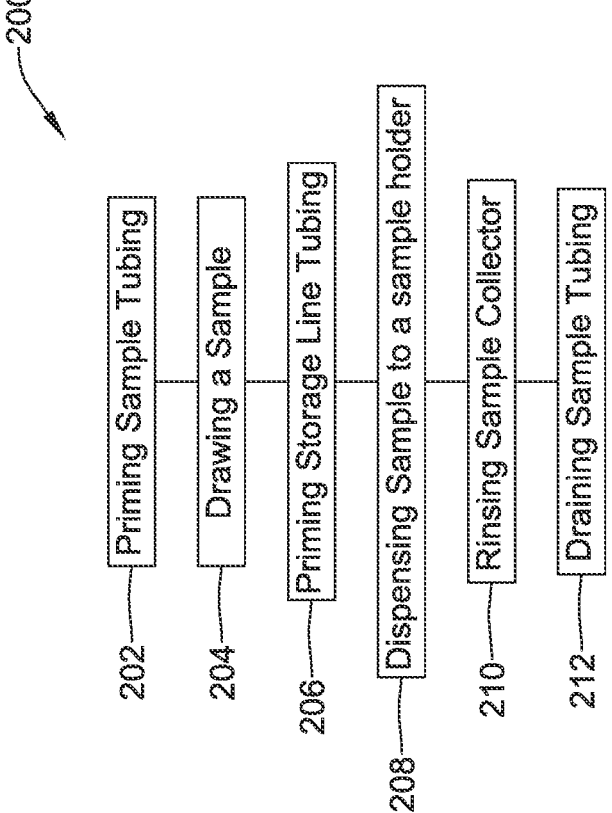
FIG. 17 is a schematic flow diagram of a technique for collecting a sample using a sample collection system.

FIG. 17 is a flow diagram of an illustrative sample collection technique 200 utilizing a sample collection system (e.g., the sample collection system 140 and/or one or more other suitable sample collection systems). Although the sample collection technique 200 may be utilized to collect various samples of fluid, the technique 200 is described below as being used to collect a sample of urine. The sample collection system used in the sample collection technique 200 may be set up with respect to a toilet and a subject may have provided urine to be sampled to a sample collector (e.g., the sample collector 90 and/or other suitable sample collector) of the sample collection system.

The technique 200 may begin by priming 202 a sample collecting line (e.g., the sample collecting tubing or line 98, 99 and/or other suitable sample collecting line). In some cases, a pump of a pumping system (e.g., the pumping system 107 and/or other suitable pumping system) may be utilized to prime the sample collecting line. In one example, a peristaltic pump and/or other suitable pump may be utilized to prime the sample collecting line.

Once the sample collecting line has been primed, the technique 200 may include drawing 204 a sample into the sample collecting line. In some cases, a pump of the pumping system may be utilized to draw sample fluid (e.g., urine, a mix of toilet water and urine, etc.) into the sample collecting line. The pump may be the same pump that was used to prime the sample collecting line and/or a different pump. In one example, a syringe pump and/or other suitable pump may be utilized to draw a predetermined or particular amount of sample fluid into the sample collecting line. An example predetermined or particular amount of sample fluid may be or may be about seven hundred fifty (750) microliters of sample fluid, but other suitable amounts are contemplated.

Using the sample fluid drawn into the sample collecting line, a storage line (e.g., the storage line 113 and/or other suitable storage line) extending to a sample storage system (e.g., the sample storage system 109 and/or other suitable sample storage system) and/or a testing tubing may be primed 206. In some cases, a pump of the pumping system may be utilized to prime the storage line with sample fluid. The pump may be the same pump that was used to draw the fluid into the sample collecting line and/or a different pump. In one example, the syringe pump and/or other suitable pump may be utilized to prime the storage line with a predetermined or particular amount of the sample fluid drawn into the sample collecting line. An example predetermined or particular amount of sample fluid used for priming the storage line may be or may be about four hundred fifty (450) microliters of sample fluid, but other suitable amounts are contemplated.

Once the storage line has been primed, the technique 200 may include providing sample fluid into the storage line and dispensing 208 the sample in and/or to a sample holder (e.g., vial and/or other suitable sample holder) of the sample storage system for storage. In some cases, a pump of the pumping system may be utilized to dispense sample fluid (e.g., urine, a mix of toilet water and urine, etc.) into the storage line and/or into the sample holder. The pump may be the same pump that was used to prime the storage line and/or a different pump. In one example, a syringe pump and/or other suitable pump may be utilized to dispense a predetermined or particular amount of the drawn sample fluid into the storage line and into the sample holder. Alternatively or additionally, the syringe pump and/or other suitable pump may be utilized to dispense a predetermined or particular amount of the drawn sample fluid into the storage line and a different pump or system (e.g., a pump or system of the sample storage system) may be utilized to dispense the drawn sample fluid into the sample holder. Other configurations for moving fluid are contemplated.

An example predetermined or particular amount of sample fluid may be or may be about three hundred (300) microliters of sample fluid, but other suitable amounts are contemplated. In some cases, the amount of sample fluid dispensed into the storage line and/or the sample holder may be a remaining portion of the drawn sample fluid after the storage line has been primed, but this is not required. An amount of sample fluid dispensed into the sample holder may be an amount that is equal to or less than the amount of sample fluid dispensed into the storage line, but this is not required.

After a sample fluid (e.g., urine and/or other suitable fluid) has been collected and sent to the sample storage system (e.g., stored at the sample storage system), the sample collector (e.g., the sample collector 90 and/or other suitable sample collector) may be rinsed 210 with a cleansing fluid. In some cases, the cleansing fluid may be water and/or other suitable fluid from a plumbing line (e.g., the plumbing line 108 and/or other suitable plumbing line) and/or a cleaning line or tube (e.g., the cleaning line 112 and/or other suitable cleaning line).

Prior to, during, and/or after rinsing the sample collector, the sample collecting line may be drained 212. In some cases, a pump of the pumping system may be utilized to drain the sample collecting line. In one example, the peristaltic pump and/or other suitable pump may be utilized to drain the sample collecting line.

Further, in some cases, the pump(s) of the pump system may be cleansed and/or rinsed along with the storage line. When cleansing and/or rinsing the pumps and/or the storage line, a predetermined amount of cleansing fluid may be drawn into the sample collecting line from the rinsing 210 of the sample collector or after rinsing the sample collector. The predetermined amount of cleansing fluid may be or may be about one (1) milliliter of cleansing fluid. Once drawn, the cleansing fluid may be expelled or dispensed into the storage line to facilitate cleaning the storage line. Illustratively, one or more pumps of the pumping system may be utilized to draw the cleansing fluid and expel the cleansing fluid into the storage line. In one example, the syringe pump and/or the peristaltic pump may be utilized to draw and expel the cleansing fluid. In some cases, the pumps of the pumping system (e.g., the peristaltic pumping system) may be utilized to expel and draw fluid through all of the fluid lines and the sample storage system to cleanse or rinse the flow paths of the sample collection system.

Figure 18:
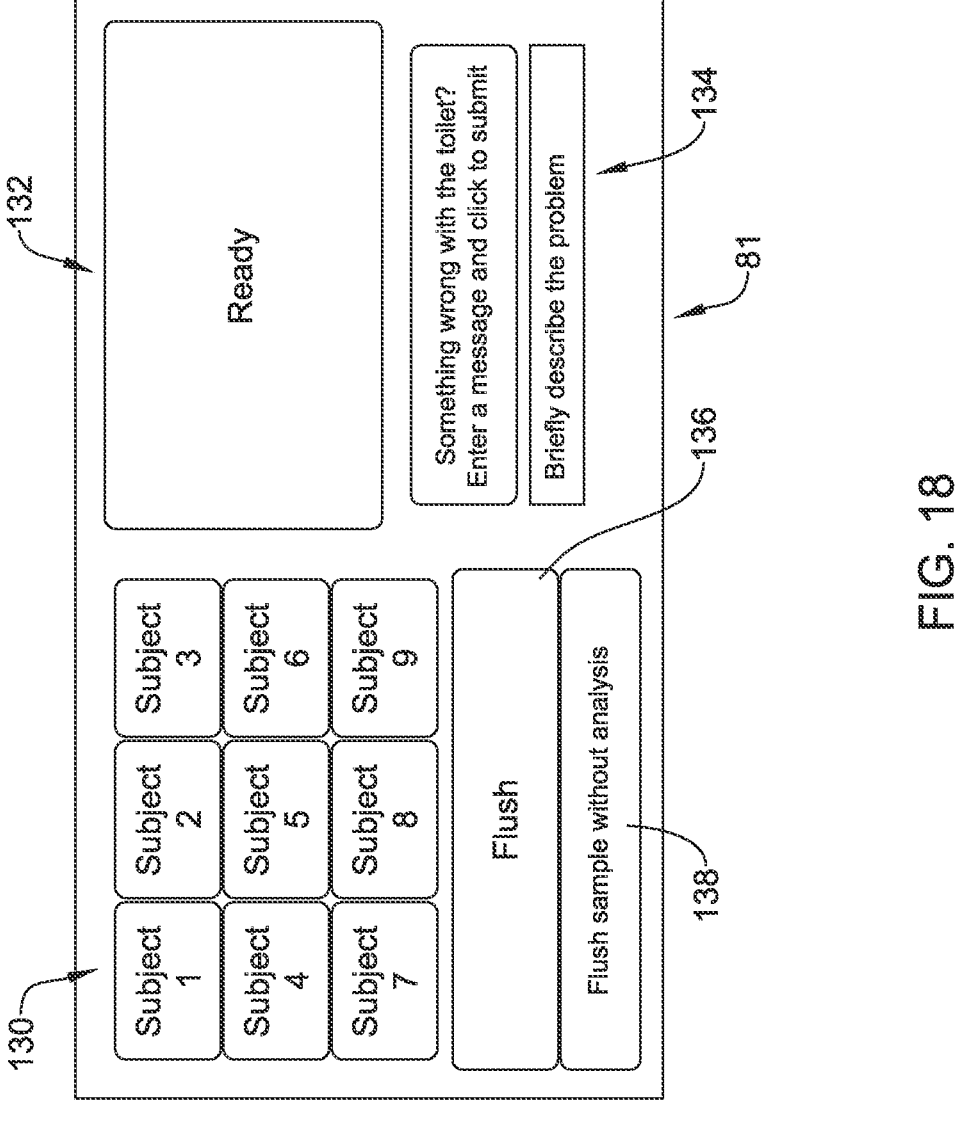
FIG. 18 is a schematic diagram of an illustrative layout for a user interface.

FIG. 18 depicts an example layout of the user interface 81 having a touchscreen display. The options displayed on the user interface 81 may include a subject selection area 130. In some cases, the subject selection area 130 may have one or more pre-set subjects having a subject number (e.g., Subject 1, Subject 2, Subject 3, and the like). Alternatively or in addition, the subject selection area 130 may include a keypad for entering a subject's PIN and/or other identification criteria. Further, layout of the user interface 81 may include a message display area 132 that may tell a subject when the toilet system is ready for use, next steps in the process, status updates, results of testing, a volume of sample obtained, and/or one or more other suitable messages. The layout may further include a messaging area 134 where the subject may enter a message to send to one or more users monitoring the toilet system, to the subject's electronic file, and/or to one or more other suitable locations. Further, the user interface 81 may include one or more flush buttons. Although not required, the user interface 81 may include a first flush button 136 that when selected initiates flushing of the toilet 10 and testing a received urine sample. In some cases, the user interface 81 may include a second flush button 138 that when selected initiates flushing of the toilet 10 without testing and/or analyzing a received urine sample.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A toilet system comprising:
a toilet, the toilet defining a basin for receiving urine from a subject;
an automated urinalysis system, the automated urinalysis system comprising:
a test material holder configured to expose a test material to a sample of urine from the subject;
a sample collection unit configured to collect a predetermined volume of the sample of urine for exposure to the test material;
an analyzer configured to receive the test material after the test material is exposed to the predetermined volume of the sample of urine;
a controller in communication with the test material holder and the analyzer,
wherein the controller is configured to determine when the test material has been exposed to the predetermined volume of the sample of urine based on a sensed current,
wherein the controller is configured to automatically cause the test material holder to provide the test material to the analyzer in response to determining the test material has been exposed to the predetermined volume of the sample of urine, and
wherein the analyzer is configured to perform a colorimetric test on the test material using one or more image capturing devices.

2. The toilet system of claim 1, wherein the analyzer comprises the one or more image capturing devices and the one or more image capturing devices are configured to image the test material after the test material has been exposed to the sample of urine.

3. The toilet system of claim 1, wherein the test material comprises one or both of a paper test strip reactive to metabolites in urine and a urinalysis test cup.

4. The toilet system of claim 1, further comprising:
a temperature sensing device configured to sense a temperature of the sample of urine.

5. The toilet system of claim 1, further comprising:
a subject sensor configured to sense a subject at or approaching the toilet; and
wherein the test material holder is configured to extend in response to the subject sensor sensing the subject at or approaching the toilet.

6. The toilet system of claim 1, wherein the controller is configured to receive an indication the test material has been exposed to the predetermined volume of the sample of urine and output a control signal to cause the test material holder to provide the test material to the analyzer for testing.

7. The toilet system of claim 1, wherein the controller is configured to output results of the analyzer testing the test material to a remote device.

8. The toilet system of claim 1, wherein the toilet is a urinal.

9. An automated urinalysis system comprising:
a test material holder configured to expose a test material to a sample of urine from a subject;
a sample collection unit configured to collect a predetermined volume of the sample of urine for exposure to the test material;
an analyzer configured to receive the test material after the test material is exposed to the predetermined volume of the sample of urine; and
a controller in communication with the test material holder and the analyzer,
wherein the controller is configured to determine when the test material has been exposed to the predetermined volume of the sample of urine based on a sensed current,
wherein the controller is configured to automatically cause the test material holder to provide the test material to the analyzer in response to determining the test material has been exposed to the predetermined volume of the sample of urine, and
wherein the analyzer is configured to perform a colorimetric test on the test material using one or more image capturing devices.

10. The automated urinalysis system of claim 9, wherein the sample collection unit includes a funnel shaped portion configured to deliver the predetermined volume of the sample of urine to the test material and cause additional urine to overflow the sample collection unit.

11. The automated urinalysis system of claim 9, further comprising:
a cartridge comprising a plurality of test materials; and
wherein a test material of the plurality of test materials is loaded onto the test material holder.

12. The automated urinalysis system of claim 9, wherein the test material holder comprises a conveyor configured to transport the test material from a sample receiving area to an analysis area.

13. The automated urinalysis system of claim 9, wherein the one or more image capturing devices comprise one or more cameras configured to capture an image of the test material.

14. The automated urinalysis system of claim 9, further comprising:

a liquid chromatography mass spectrometry (LCMS) unit;

a sample flow path in fluid communication with the LCMS unit and the sample collection unit; and wherein the LCMS unit is configured to withdraw a predetermined amount of sample fluid from the sample flow path and perform an analysis on the predetermined volume of the sample of urine.

15. The automated urinalysis system of claim 14, further comprising:

a pump configured to pump the sample of urine from the sample collection unit through the sample flow path.

16. The automated urinalysis system of claim 14, further comprising:

a valve system in communication with the sample flow path and configured to control a flow of sample fluid to the LCMS unit.

17. The automated urinalysis system of claim 9, wherein the analyzer is configured to perform the colorimetric test on an optical image of the test material captured using the one or more image capturing devices.

18. The automated urinalysis system of claim 17, wherein the controller is configured to cause the optical image to be stored in a database.

19. An automated urinalysis system comprising:

a test material holder configured to expose a test material to a sample of urine from a subject;

a sample collection unit configured to collect a predetermined volume of the sample of urine for exposure to the test material;

an analyzer configured to receive the test material after the test material is exposed to the predetermined volume of the sample of urine; and a controller in communication with the test material holder and the analyzer, wherein the controller is configured to determined when the test material has been exposed to the predetermined volume of the sample of urine based on a sensed current, wherein the controller is configured to automatically cause the test material holder to provide the test material to the analyzer in response to determining the test material has been exposed to the predetermined volume of the sample of urine, and wherein the sample collection unit includes a funnel shaped portion configured to deliver the predetermined volume of the sample of urine to the test material and cause additional urine to overflow the sample collection unit.

\* \* \* \* \*